US008806920B2

(12) United States Patent
Blekher et al.

(10) Patent No.: US 8,806,920 B2
(45) Date of Patent: Aug. 19, 2014

(54) CO-MOLDED PIERCEABLE STOPPER AND METHOD FOR MAKING THE SAME

(75) Inventors: Alex Blekher, Sussex, NJ (US); Bradley M. Wilkinson, North Haledon, NJ (US); Craig Owen Russ, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 561 days.

(21) Appl. No.: 12/398,628

(22) Filed: Mar. 5, 2009

(65) Prior Publication Data

US 2009/0308184 A1    Dec. 17, 2009

Related U.S. Application Data

(60) Provisional application No. 61/033,966, filed on Mar. 5, 2008.

(51) Int. Cl.
*G01N 11/00* (2006.01)
*A61B 5/15* (2006.01)
*B65D 51/00* (2006.01)

(52) U.S. Cl.
CPC ............ B65D 51/002 (2013.01); A61B 5/1411 (2013.01); B65D 2221/00 (2013.01)
USPC ....................................................... 73/53.01

(58) Field of Classification Search
USPC ..................................................... 73/864.41
See application file for complete search history.

(56) References Cited

U.S. PATENT DOCUMENTS

| 2,393,578 A | 1/1946 | Waite |
| 2,594,621 A | 4/1952 | Derrick |
| 2,698,272 A | 12/1954 | Clapp et al. |
| 2,998,726 A * | 9/1961 | Peterson .................... 73/864.66 |
| 3,136,440 A | 6/1964 | Krug et al. |
| 3,297,184 A | 1/1967 | Andelin |
| 3,430,798 A * | 3/1969 | Goyet et al. .................. 215/295 |
| 3,552,591 A | 1/1971 | Wimmer |
| 3,680,605 A * | 8/1972 | Nigro ............................. 141/20 |
| 3,760,969 A | 9/1973 | Shimamoto et al. |
| 4,163,500 A | 8/1979 | Gunne et al. |
| 4,201,209 A | 5/1980 | LeVeen et al. |
| 4,226,333 A | 10/1980 | Percarpio |
| 4,227,620 A | 10/1980 | Conway |
| 4,259,956 A | 4/1981 | Ogle |
| 4,308,232 A | 12/1981 | Crouther et al. |
| 4,381,275 A | 4/1983 | Sorensen |

(Continued)

FOREIGN PATENT DOCUMENTS

| EP | 0740155 A1 | 10/1996 |
| JP | 03-133610 A | 6/1991 |
| JP | 03-142209 A | 6/1991 |
| JP | 2001-245958 A | 9/2001 |

*Primary Examiner* — Peter Macchiarolo
*Assistant Examiner* — Alex DeVito
(74) *Attorney, Agent, or Firm* — The Webb Law Firm

(57) ABSTRACT

A closure and method of making a closure are disclosed. The closure includes a cap body having a top portion and an opening extending therethrough defining a cavity in communication with said opening. A flow channel is defined within a portion of the cap body having an inlet and an outlet. A stopper is disposed within the cavity adjacent the outlet of the flow channel. The stopper is formed from a material adapted for flowing through the flow channel to form a pierceable portion, with at least one of the cap body and the stopper configured for closing a container.

43 Claims, 31 Drawing Sheets

(56) References Cited

U.S. PATENT DOCUMENTS

| | | |
|---|---|---|
| 4,397,318 A * | 8/1983 | Burns .................... 600/576 |
| 4,411,163 A | 10/1983 | White |
| 4,508,676 A | 4/1985 | Sorensen |
| 4,512,486 A | 4/1985 | Kobayashi et al. |
| 4,524,880 A | 6/1985 | Danielson et al. |
| 4,576,185 A | 3/1986 | Proud et al. |
| 4,635,807 A | 1/1987 | Knapp |
| 4,682,703 A | 7/1987 | Kasai et al. |
| 4,724,028 A | 2/1988 | Zabielski et al. |
| 4,803,031 A | 2/1989 | Ochs et al. |
| 4,805,635 A | 2/1989 | Korf et al. |
| 4,869,384 A | 9/1989 | Ogle, II |
| 4,893,636 A | 1/1990 | Cook et al. |
| 4,967,919 A | 11/1990 | Earhart |
| 4,982,614 A * | 1/1991 | Gora .................... 73/863.81 |
| 5,019,243 A | 5/1991 | McEwen et al. |
| 5,060,812 A | 10/1991 | Ogle, II |
| 5,078,941 A | 1/1992 | Tatsumi et al. |
| 5,215,102 A | 6/1993 | Guirguis |
| 5,217,668 A | 6/1993 | Matsuzaki et al. |
| 5,232,109 A | 8/1993 | Tirrell et al. |
| 5,279,606 A | 1/1994 | Haber et al. |
| 5,286,453 A | 2/1994 | Pope |
| 5,288,466 A | 2/1994 | Burns |
| 5,379,907 A | 1/1995 | Niedospial et al. |
| 5,384,096 A | 1/1995 | Burns |
| 5,393,674 A | 2/1995 | Levine et al. |
| 5,456,886 A | 10/1995 | Burns |
| 5,458,113 A | 10/1995 | Burns |
| 5,458,854 A | 10/1995 | Burns |
| 5,484,566 A | 1/1996 | Gabbard |
| 5,522,518 A | 6/1996 | Konrad et al. |
| 5,527,513 A | 6/1996 | Burns |
| 5,552,117 A | 9/1996 | Burns |
| 5,632,396 A | 5/1997 | Burns |
| 5,651,998 A | 7/1997 | Bertschi et al. |
| 5,714,125 A | 2/1998 | Sagstetter |
| 5,716,683 A | 2/1998 | Harvey et al. |
| 5,738,233 A | 4/1998 | Burns |
| 5,779,074 A | 7/1998 | Burns |
| 5,785,925 A | 7/1998 | U'Ren |
| 5,789,033 A | 8/1998 | Bertschi et al. |
| 5,798,069 A | 8/1998 | Bertschi et al. |
| 5,902,276 A | 5/1999 | Namey, Jr. |
| 6,019,751 A | 2/2000 | Gabbard et al. |
| 6,030,582 A | 2/2000 | Levy |
| 6,071,454 A | 6/2000 | Shimizu et al. |
| 6,074,612 A | 6/2000 | Sagstetter |
| 6,165,402 A | 12/2000 | Gabbard et al. |
| 6,234,335 B1 | 5/2001 | Gee et al. |
| 6,322,739 B1 | 11/2001 | Andersson et al. |
| 6,361,744 B1 | 3/2002 | Levy |
| 6,426,049 B1 | 7/2002 | Rosen et al. |
| 6,503,453 B1 | 1/2003 | Sagstetter |
| 6,524,295 B2 | 2/2003 | Daubert et al. |
| 6,562,300 B2 | 5/2003 | Rosen et al. |
| 6,607,685 B2 | 8/2003 | Naritomi et al. |
| 6,610,041 B2 | 8/2003 | Daubert et al. |
| 6,635,043 B2 | 10/2003 | Daubert et al. |
| 6,686,204 B2 | 2/2004 | Dubrowny et al. |
| 6,716,396 B1 | 4/2004 | Anderson et al. |
| 6,720,044 B2 | 4/2004 | Andersson et al. |
| 6,727,101 B1 | 4/2004 | Sagstetter |
| 6,752,965 B2 | 6/2004 | Levy |
| 6,806,094 B2 | 10/2004 | Anderson et al. |
| 6,821,789 B2 | 11/2004 | Augello et al. |
| 6,893,612 B2 | 5/2005 | Kacian et al. |
| 6,939,514 B1 | 9/2005 | Mayes |
| 7,022,289 B1 | 4/2006 | Schlein et al. |
| 7,028,858 B2 | 4/2006 | Auer et al. |
| 7,097,057 B2 | 8/2006 | Classens |
| 7,137,519 B2 | 11/2006 | Becker |
| 7,198,757 B2 | 4/2007 | Chiarin |
| 7,210,593 B2 | 5/2007 | Stull et al. |
| 7,276,383 B2 | 10/2007 | Iheme et al. |
| 7,294,308 B2 | 11/2007 | Kacian et al. |
| 7,309,468 B2 | 12/2007 | Stevens et al. |
| 7,309,469 B2 | 12/2007 | Anderson et al. |
| 7,334,310 B2 | 2/2008 | Becker |
| 7,374,802 B2 | 5/2008 | Zihlmann |
| 7,435,389 B2 | 10/2008 | Anderson et al. |
| 2003/0028154 A1 | 2/2003 | Ross |
| 2003/0039717 A1 | 2/2003 | Hwang et al. |
| 2003/0133844 A1 | 7/2003 | Conway |
| 2004/0006330 A1 | 1/2004 | Fangrow, Jr. |
| 2004/0043505 A1 | 3/2004 | Walenciak et al. |
| 2004/0045924 A1 | 3/2004 | Naritomi et al. |
| 2004/0118803 A1 | 6/2004 | Claessens |
| 2004/0149287 A1 | 8/2004 | Namey, Jr. |
| 2005/0059161 A1 | 3/2005 | Anderson et al. |
| 2005/0090766 A1 | 4/2005 | Montanari |
| 2006/0068206 A1 | 3/2006 | Hala et al. |
| 2006/0089602 A1 | 4/2006 | Boucherie |
| 2006/0175280 A1 | 8/2006 | Anraku et al. |
| 2006/0200968 A1 | 9/2006 | Thilly et al. |
| 2007/0173783 A1 | 7/2007 | Haindl |
| 2007/0267776 A1 | 11/2007 | Conard et al. |
| 2008/0047908 A1 | 2/2008 | Sekine et al. |
| 2008/0072690 A1 | 3/2008 | Kacian et al. |
| 2008/0110846 A1 | 5/2008 | Anderson et al. |
| 2008/0152545 A1 | 6/2008 | Anderson et al. |
| 2008/0245163 A1 | 10/2008 | Iheme et al. |
| 2008/0274514 A1 | 11/2008 | Dickey et al. |
| 2008/0277370 A1 | 11/2008 | Mikkelsen |

* cited by examiner

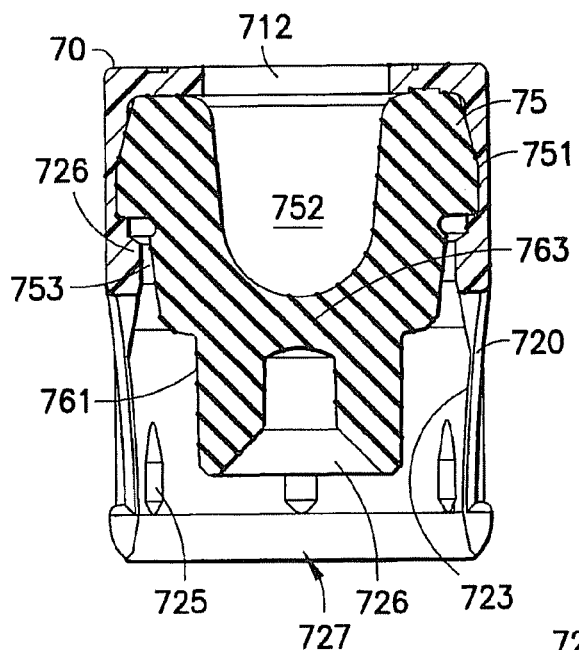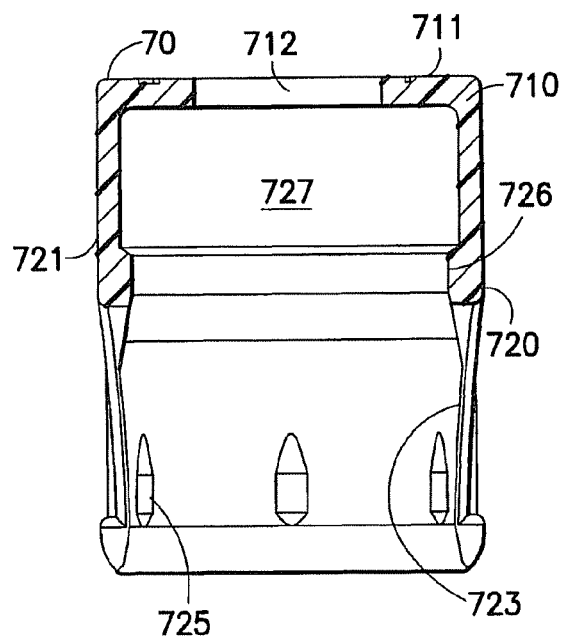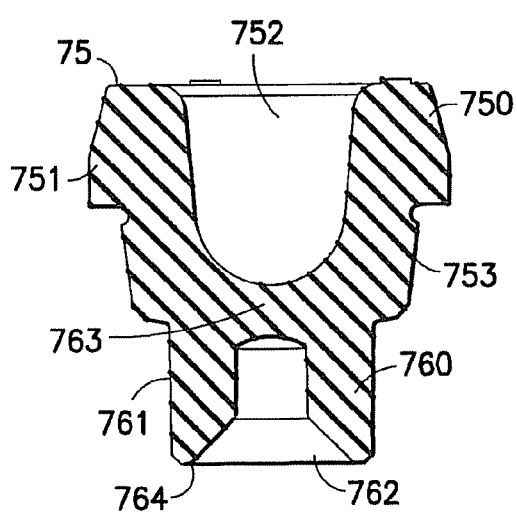

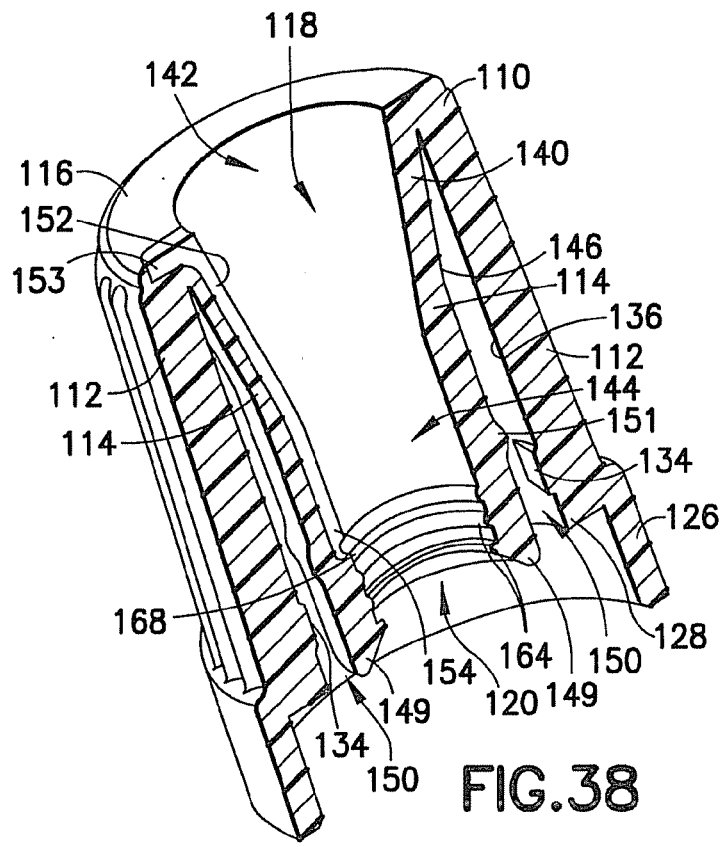
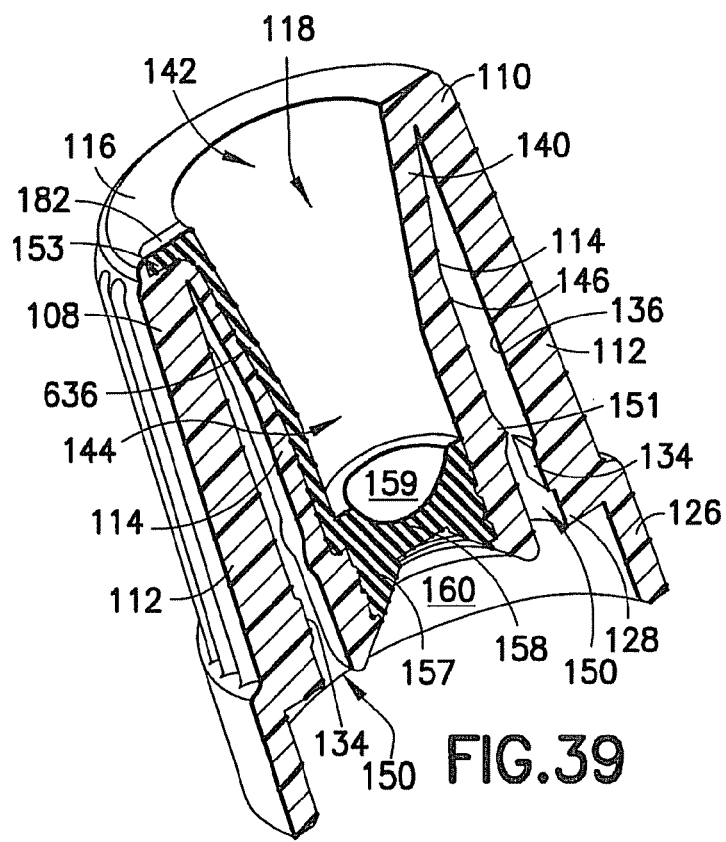

CO-MOLDED PIERCEABLE STOPPER AND METHOD FOR MAKING THE SAME

CROSS REFERENCE TO RELATED APPLICATION

This application claims priority to U.S. Provisional Patent Application No. 61/033,966, filed Mar. 5, 2008, entitled "Device for Capillary Collection of Blood Samples", the entire disclosure of which is herein incorporated by reference.

BACKGROUND OF THE INVENTION

1. Field of the Invention

The present invention relates to a device for the collection, storage, and transfer of a blood or specimen sample obtained from a patient for medical diagnostic testing. More specifically, the present invention relates to a device for capillary collection of blood samples from a skin surface of the patient. The device includes a collection tube having a lip feature surrounding a top opening of the tube suitable for collecting samples from a skin surface. The device also includes a cap assembly having a stopper for closing and sealing the tube after the blood or specimen sample has been collected. The stopper incorporates space elimination features to funnel the blood or specimen sample to a probe assembly of a testing instrument during transfer from the collection tube.

2. Description of Related Art

Conventional capillary collection devices according to the prior art typically provide a microtube or collection container having a raised receiving lip or funnel feature that engages the skin surface of a patient that has been pierced so as to draw a blood sample from the capillaries located just beneath the skin surface. The internal collection cavities of such prior art collection containers are typically straight-walled and provide no features for promoting the flow of drawn blood into the cavity during collection or the flow of blood to the testing instrument during transfer. Thus a significant amount of the collected blood or specimen sample is caught on the sidewall of the cavity due to surface tension during collection and during transfer.

After collection, these tubes are sealed by a cap assembly disposed on the collection container. Conventional cap assemblies provide a flat bottom surface in communication with the collection cavity. As a result, a significant amount of dead volume of sample is created within the collection cavity during transfer since neither the collection container nor the cap assembly adequately funnel or channel the collected blood sample to the aspiration hole of the probe needle. As can be appreciated, conventional prior art collection devices create a significant amount of wasted sample and require a significantly higher volume of sample to be collected than what is actually needed to perform the diagnostic tests for which the sample is being collected. Sample volumes are particularly important in capillary applications, where a very small volume of blood is typically collected and/or available, and therefore avoiding any waste is particularly important.

SUMMARY OF THE INVENTION

In accordance with an embodiment of the present invention, a closure includes a cap body having a top portion and an opening extending therethrough defining a cavity in communication with said opening. A flow channel is defined within a portion of the cap body and has an inlet and an outlet. A stopper is disposed within the cavity adjacent the outlet of the flow channel, with the stopper formed from a material adapted for flowing through the flow channel to form a pierceable portion. At least one of the cap body and the stopper are configured for closing a container.

The cap body may be formed from a first molding material and the stopper may be formed from a pierceable second molding material, the second molding material being different than the first molding material. The flow channel inlet may extend toward the top portion. The inlet of the flow channel may be offset with respect to a longitudinal centerline extending through the cavity of the closure. The stopper may have a bottom surface and a conical recess defined within the stopper forming the pierceable portion. The conical recess may be in communication with an interior of a container when the closure closes a container.

The stopper may also be positioned within the cavity at a predetermined location such that a distance between the top portion and the conical recess corresponds to a distance between a probe contact surface and an aspiration hole of a probe assembly. The bottom surface may have a conical shape such that the pierceable portion has an area of reduced thickness as compared to the thickness of another portion of the stopper. Optionally, the pierceable portion may include a star shape to facilitate piercing thereof. The cap body may be formed from a high density polyethylene and the stopper is formed from a thermoplastic elastomer. In another configuration, a plurality of gripping members are disposed in connection with an outer surface of the external annular skirt.

In accordance with another embodiment of the present invention, a closure includes a cap body having a top portion and an opening extending therethrough. An external annular skirt may depend from an outer perimeter of the top portion, and an internal annular skirt may depend from an inner portion of the top portion adjacent the opening with the internal annular skirt defining a cavity in communication with the opening in the top portion. A flow channel may be defined within a portion of the internal annular skirt having an inlet adjacent the top portion and an outlet. A stopper may be disposed within the cavity adjacent the outlet of the flow channel, with the stopper formed from a material adapted for flowing through the flow channel to form a pierceable portion. At least one of the cap body and the stopper are configured for closing a container.

The flow channel inlet may extend through the top portion. The flow channel may also extend within an interior surface of the internal annular skirt. The stopper may be co-formed with a portion of an interior surface of the internal annular skirt. In one configuration, the internal annular skirt includes a ramped portion defining a funnel-shaped cavity having a larger diameter adjacent the top portion and a smaller diameter adjacent the stopper. A bottom surface of the internal annular skirt may include at least one protrusion extending into the cavity to join the second molding material to the first molding material.

In accordance with another embodiment of the present invention, a container assembly includes a collection container having a closed bottom, an open top portion, and a sidewall extending therebetween adapted to receive a specimen sample therein. The closure includes a cap body having a top portion and an opening extending therethrough defining a cavity in communication with said opening. The closure also includes a flow channel defined within a portion of the cap body having an inlet and an outlet. The closure further includes a stopper disposed within the cavity adjacent the outlet of the flow channel, wherein the stopper is formed from a material adapted for flowing through the flow channel to form a pierceable portion. At least one of the cap body and the stopper are configured for closing the open top portion of the container.

The inlet of the flow channel may be offset with respect to a longitudinal centerline extending through the cavity of the cap assembly. A top portion of the sidewall of the collection container may include a collection lip funnel for facilitating flow of a sample into an interior of the collection container. The cap body may include an external annular skirt and an internal annular skirt extending from the top portion, defining a channel therebetween configured for receiving the top portion of the sidewall and the collection lip funnel therein. In another configuration, the closure includes at least one downwardly extending ramp member, and the collection container includes at least one upwardly extending ramp member configured for cooperating with the at least one downwardly extending ramp member to engage or disengage the closure with the collection container.

A conical recess may be included within the stopper, such that the conical recess is in communication with an interior of the collection container when the closure closes the open top portion of the collection container. The stopper may define a conical recess extending between a bottom surface and the pierceable portion, and a sampling distance may extend between a top surface of the top portion of the cap body and an apex of the conical recess, such that it is adapted to position an aspiration hole of a probe assembly at the apex of the conical recess during withdrawal of a specimen from the collection cavity. In a further configuration, the collection container defines an interior having at least one capillary channel disposed therein. The pierceable portion of the closure may be pierceable by a cannula while the closure closes the open top end of the collection container. Further, the pierceable portion may be adapted to remove vestige from the cannula upon withdrawal of the cannula from an interior of the collection container.

In accordance with yet another embodiment of the present invention, a method of forming a pierceable cap assembly for a container includes the step of providing a mold having a molding cavity. The method also includes the step of injecting a first molding material into the molding cavity to form a cap body having a top portion, an opening extending therethrough, and a cavity in communication with the opening, the outer cap having a flow channel extending from the top portion of the outer cap to a target location within the cavity. The method further includes the step of injecting a second molding material into the flow channel such that the second molding material flows through the flow channel to the target location, wherein the second molding material forms a pierceable septum within the cavity of the cap body.

The first molding material may form an external annular skirt and an internal annular skirt, each depending from the top portion, wherein at least a portion of the internal annular skirt defines the target location. The second molding material may be injected from a location which is offset with respect to a longitudinal centerline extending through the target location. The flow channel may extend along the vertical height of an interior wall surface of the internal annular skirt. The internal annular skirt may optionally include at least one protrusion adjacent the target location. The second molding material may flow to the target location to form a bond with the at least one protrusion. In another configuration, the second molding material flows to the target location to form a star-shaped septum with the at least one protrusion to facilitate piercing of the septum.

Optionally, the first molding material is high density polyethylene and said second molding material is a thermoplastic elastomer. The method may further include a first gate for injection of the first molding material and a second gate for injection of the second molding material. The second gate may be positioned adjacent the top portion of the cap body at an inlet of the flow channel. The second gate may also be positioned at approximately 180° with respect to the first gate. In a further configuration, after injection of the second material, at least a portion of the second molding material may remain within the flow channel. A closure made by the method described above is also provided herein.

In accordance with yet another embodiment of the present invention, a method of forming a two-shot molded closure includes the step of supplying a first molding material into a mold to form a cap body having an interior wall surface and a flow channel defined therein, the flow channel having an inlet and an outlet. The method also includes the step of supplying a second molding material into the mold at a location adjacent to the inlet of the flow channel such that at least a portion of the second molding material flows through the outlet to a target location to form a septum. The inlet of the flow channel may be remote from the target location.

Optionally, the inlet of the flow channel may be offset with respect to a longitudinal centerline extending through the target location. A closure made by the method described above is also provided herein.

In accordance with yet another embodiment of the present invention, a method of forming a closure for a container includes the step of injecting a first molding material into a mold to form a cap body defining a center portion. The method also includes the step of injecting a second molding material into the mold to form a pierceable septum within the center portion of the cap body. The second molding material may be injected from a location that is offset with respect to a longitudinal centerline extending through the center portion. Optionally, the cap body includes a flow channel extending therethrough. The second molding material may flow through the flow channel to form the pierceable septum. A closure made by the method described above is also provided herein.

Further, in accordance with yet another embodiment of the present invention, a method for accessing a sample contained within a collection container, the collection tube being sealed by a stopper having a pierceable closure and a conical recess in communication with an interior defined within the collection container, includes the step of positioning the stopper and collection container on a probe assembly at an angled inverted orientation. The method also includes the step of inserting the probe assembly into the collection container such that a probe needle pierces the pierceable closure of the stopper and an aspiration hole of the probe needle becomes disposed within the conical recess. The method also includes the step of funneling a sample from the cavity into the aspiration hole of the probe needle via the conical recess.

The method may also include the step of restraining a portion of the probe needle at a sampling distance of the collection container to position the aspiration hole of the probe needle adjacent an apex of the conical recess. The sampling distance may be from 0.58 to 0.60 inches.

In another embodiment, the specimen collection assembly includes an outer cap having a top portion and an annular skirt portion depending from the top portion, the top portion having an opening extending therethrough and defining a cavity. A stopper may be disposed within the cavity having a bottom surface, a pierceable closure, and a conical recess defined within the stopper extending from the bottom surface of the stopper to the pierceable closure. A collection container may include a top opening and an exterior sidewall defining a collection cavity, with the cap assembly engageable with the collection tube such that the annular skirt portion engages the exterior sidewall of the collection tube with the stopper extending into the collection cavity so as to sealingly engage the sidewall of the collection cavity with the conical recess of the stopper being in communication with the collection cavity.

The collection container may include a lip feature including a plurality of raised portions and a plurality of lowered portions in an alternating arrangement about the top opening. The collection container may also include a collection funnel adjacent the top opening, and the outer cap may define an opening for receiving the collection funnel therein when the outer cap is engaged with a portion of the collection container. The stopper may further include at least one capillary channel extending along at least a portion of the conical recess. Optionally, the collection container may also include at least one capillary channel extending along a portion of an interior of the exterior sidewall. In another configuration, the stopper may include at least one capillary channel extending along at least a portion of the conical recess and aligned with at least one capillary channel extending along a portion of the interior of the exterior sidewall of the collection container.

In another embodiment of the present invention, a specimen collection container includes a top opening and an exterior sidewall defining a collection cavity, and a lip feature substantially surrounding the top opening. The lip feature may include two opposing raised portions and two opposing lowered portions offset from the opposing raised portions, in which the lip feature is contoured to engage a skin surface from which a sample is being extracted.

The top opening may be adapted to engage a stopper to seal the top opening and collection cavity.

In another embodiment, a specimen collection assembly includes an outer cap having a top portion and an annular skirt portion depending from the top portion defining a cut out portion. The top portion may have an opening extending therethrough defining a cavity. A collection container may include a top opening and an exterior sidewall defining a collection cavity. At least a portion of the outer cap may be engageable with a portion of the collection container to seal the top opening.

Optionally, the cut out portion has an elliptical or parabolic shape. In another configuration, the cut out portion provides visual verification of a connection between the outer cap and the collection container. In another configuration, the assembly further includes a stopper disposed within the cavity having a bottom surface, a pierceable closure, and a conical recess defined within the stopper extending from the bottom surface of the stopper to the pierceable closure. The cap assembly may engage the collection tube such that the annular skirt portion engages the exterior sidewall of the collection tube with the stopper extending into the collection cavity so as to sealingly engage the sidewall of the collection cavity with the conical recess of the stopper being in communication with the collection cavity.

The stopper may be integrally formed with the outer cap. The stopper may also include at least one capillary channel extending along at least a portion of the conical recess. The collection container may also include at least one capillary channel extending along a portion of an interior of the exterior sidewall. In another configuration, the stopper may include at least one capillary channel extending along at least a portion of the conical recess and aligned with at least one capillary channel extending along a portion of the interior of the exterior sidewall of the collection container.

In another embodiment of the present invention, a specimen collection assembly includes an outer cap having a top portion and an annular skirt portion depending from the top portion, the top portion having an opening extending therethrough and defining a cavity. A stopper may be disposed within the cavity having a bottom surface, a pierceable closure, and a conical recess defined within the stopper extending from the bottom surface of the stopper to the pierceable closure. A collection container may include a top opening and an exterior sidewall defining a collection cavity adapted to receive a specimen therein, with at least a portion of one of the outer cap and the stopper engageable with the collection container to seal the top opening. The stopper may be molded within the cavity such that a sampling distance extending between a top surface of the top portion of the outer cap and an apex of the conical recess is adapted to position an aspiration hole of a probe assembly at the apex of the conical recess during withdrawal of a specimen from the collection cavity.

Optionally, the stopper includes at least one capillary channel extending along at least a portion of the conical recess. The collection container may also include at least one capillary channel extending along a portion of an interior of the exterior sidewall. The sampling distance may be from 0.58 to 0.60 inches.

Further details and advantages of the invention will become clear upon reading the following detailed description in conjunction with the accompanying drawing figures, wherein like parts are designated with like reference numerals throughout.

BRIEF DESCRIPTION OF THE DRAWINGS

FIG. 15 is a vertical cross-sectional view of the cap assembly shown in FIG. 14 in an assembled state.

FIG. 16 is a vertical cross-sectional view of the outer cap of the cap assembly shown in FIG. 14.

FIG. 17 is a vertical cross-sectional view of the stopper of the cap assembly shown in FIG. 14.

FIG. 38 is a cross-sectional perspective view of first shot of molded material for the cap assembly shown in FIG. 30.

FIG. 39 is a cross-sectional perspective view of a second shot of molded material for the cap assembly shown in FIG. 30.

DESCRIPTION OF PREFERRED EMBODIMENTS

For purposes of the description hereinafter, spatial orientation terms, if used, shall relate to the referenced embodiment, as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Figure 1:
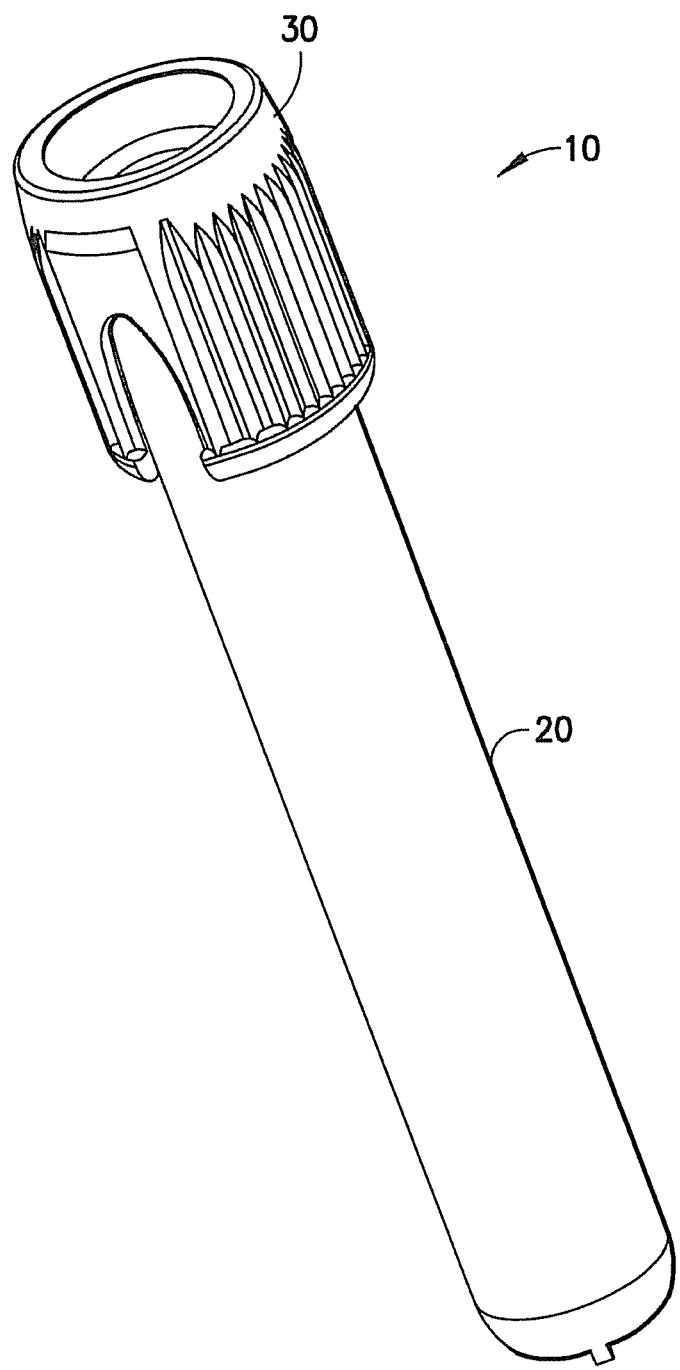
FIG. 1 is a perspective view of a device for capillary collection of blood samples pursuant to a first embodiment of the present invention.
Figure 2:
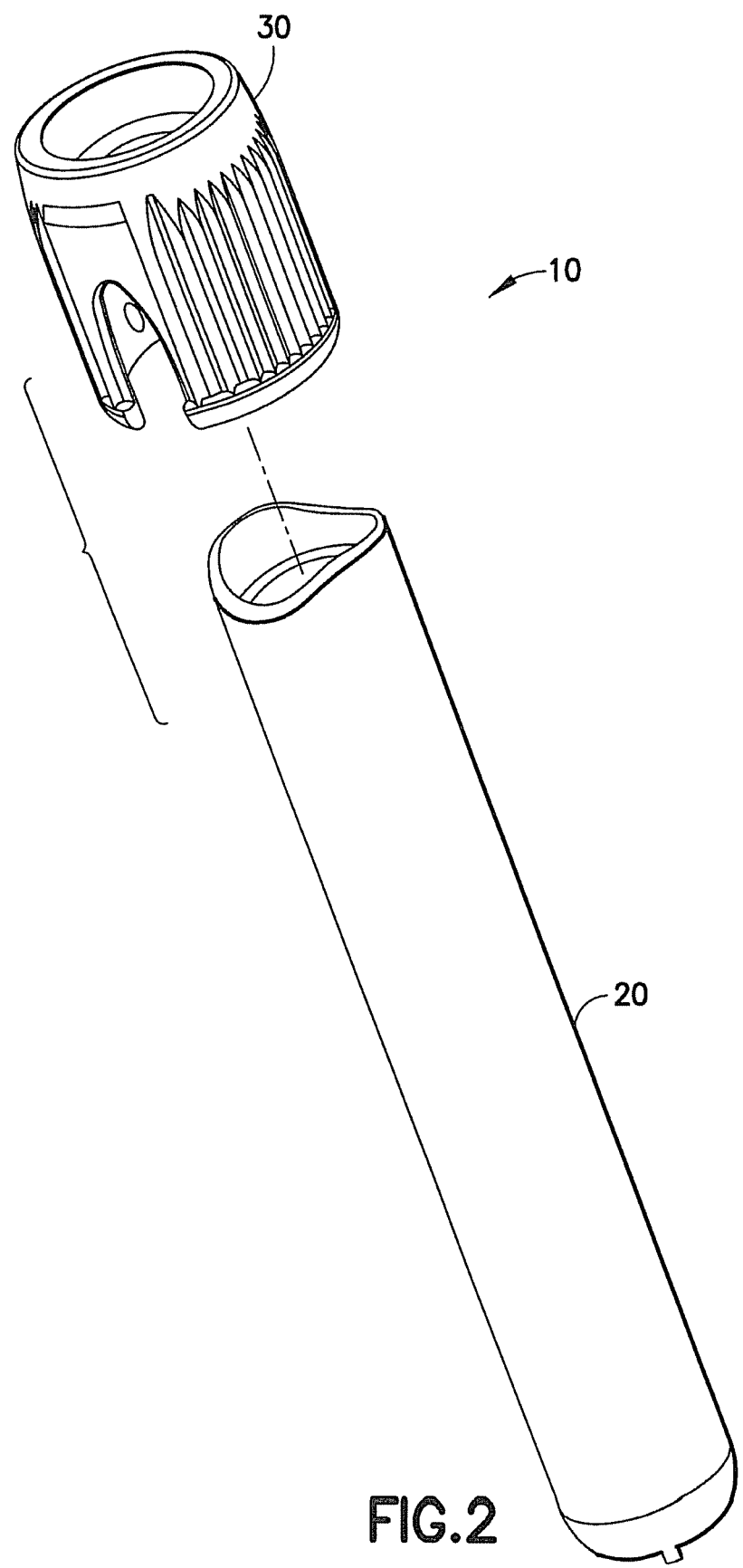
FIG. 2 is an exploded perspective view of the capillary collection device shown in FIG. 1.

Referring to FIGS. 1 and 2, a collection device 10 according to a first embodiment of the present invention is shown. Collection device 10 includes a collection tube 20 for the collection, storage, and eventual transfer of biological specimens, including blood samples, for purposes of diagnostic testing. A cap assembly 30 is disposed on the collection tube 20 so as to cover and seal the collection tube 20 and any sample contained therein. According to the embodiment shown, cap assembly 30 is removably disposed and attached to the collection tube 20 after collection of the sample contained therein.

The collection tube 20 may be a biological specimen collection container for proteomics, molecular diagnostics, chemistry sampling, blood or other bodily fluid collection, coagulation sampling, hematology sampling, and the like. In one embodiment, the collection tube 20 can be particularly suited for receipt and storage of a bodily fluid specimen. In a further embodiment, the collection tube 20 is particularly suited for receipt and storage of blood, such as venous blood or capillary blood, from a patient. As used herein, the term "patient" means a mammalian organism, and the collection tube 20 of the present invention is intended for use in specimen collection procedures performed on humans and/or animals.

Figure 3:
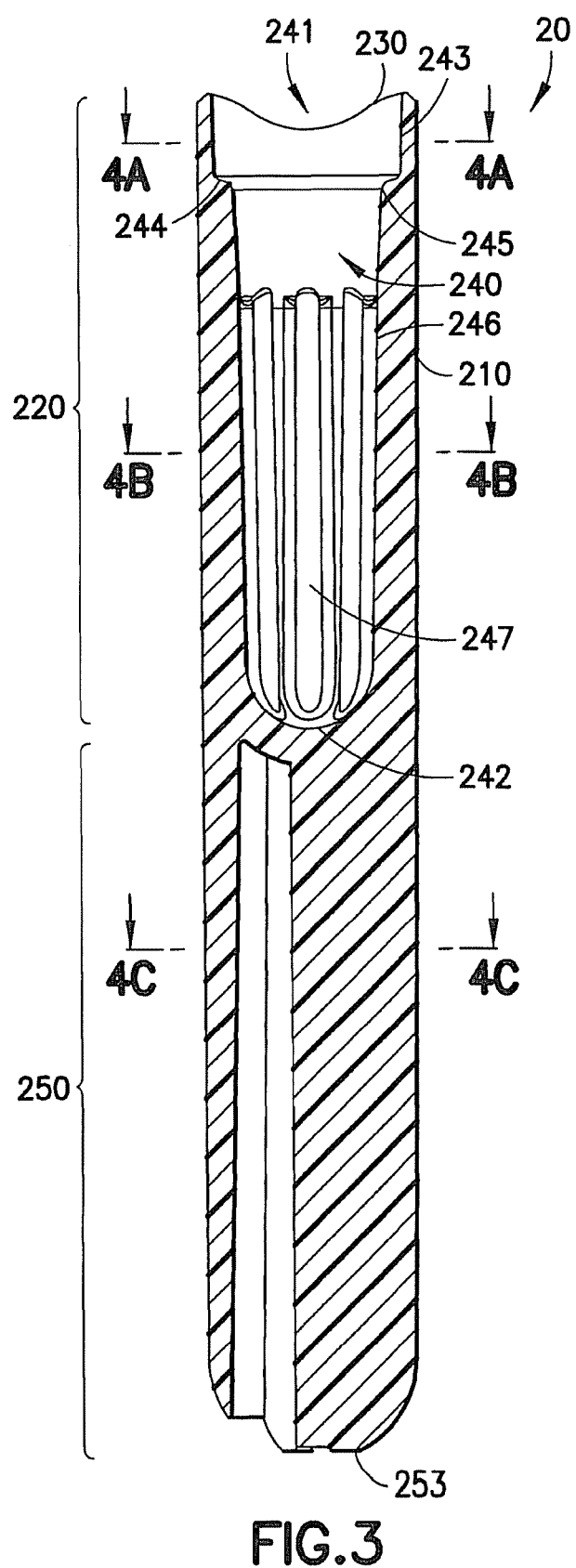
FIG. 3 is a vertical cross-sectional view of the collection tube shown in FIGS. 1 and 2.

As shown in FIG. 3, collection tube 20 is a microtube suited for capillary collection of blood samples having exterior dimensions conforming to a standard 13×75 mm tube so as to be compatible with standard testing instruments. Collection tube 20 is formed, such as by injection molding, from suitable plastic or composite material as is known to be suitable by those of ordinary skill in the art. Collection tube 20 is defined by an exterior sidewall 210 extending from a rounded tube bottom 253 to a lip portion 230. Collection tube 20 includes upper portion 220 and lower portion 250.

Figure 6:
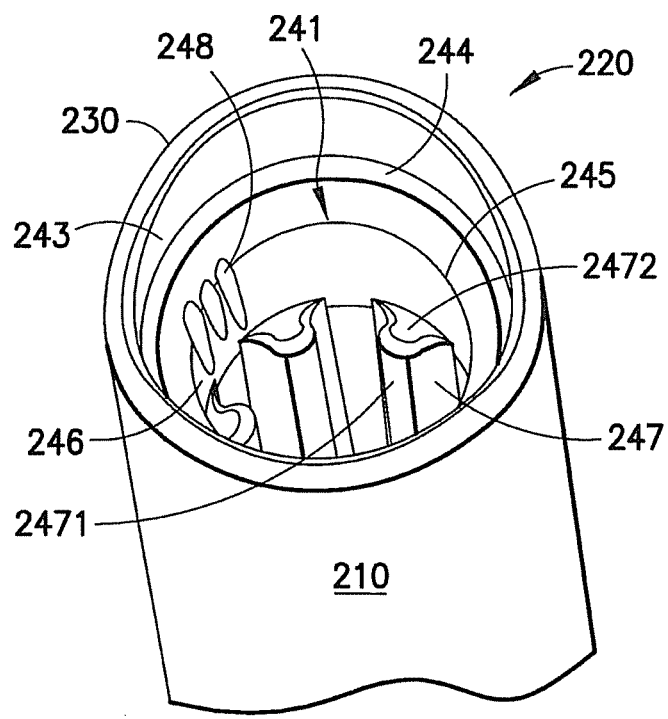
FIG. 6 is a detailed elevated perspective view of area "A", shown in FIG. 5.

Upper portion 220 of collection tube 20 defines an internal cavity 240 for the collection, containment, and eventual transfer of biological specimens. Internal cavity 240 extends through the upper portion 220 of the collection tube 20 from a rounded bottom 242 to a top opening 241 in the collection tube 20. Internal cavity 240 of collection tube 20 may be coated with an additive sprayed into the collection tube 20 for preserving a blood or specimen sample contained within the collection tube 20 during storage or for other diagnostic purposes as is known by those of ordinary skill in the art. As shown in FIG. 6, the top opening 241 is surrounded by lip portion 230.

Figure 4A:
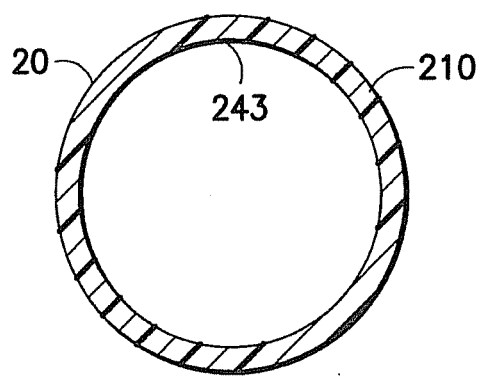
FIGS. 4A, 4B, and 4C are horizontal cross-sectional views of the collection tube taken along lines 4A-4A, 4B-4B, and 4C-4C, shown in FIG. 3, respectively.

With reference to FIGS. 3 and 6, internal cavity 240 is defined within the upper portion 220 of the collection tube 20 by a plurality of sidewall surfaces 243, 244, 245, and 246 and has a generally tapered and rounded profile defining a funnel shape. As shown in FIG. 4A, a first sidewall surface 243 of internal cavity 240 defines a smooth, cylindrical surface so as to promote the unobstructed flow of specimen from the top opening 241 further into the internal cavity 240. The distance between the first sidewall surface 243 of the internal cavity 240 and the exterior sidewall surface 210 is preferably small so as to allow for a suitably wide top opening 241 for collection of a blood or specimen sample.

Preferably, internal cavity 240 has an overall increased height to diameter ratio so as to create a taller column of blood or specimen within the collection tube 20. Providing a taller column of blood or specimen makes it easier for a medical professional or diagnostician to discern the volume of blood or specimen contained within the collection tube 20 in order to determine the amount of blood or specimen collected or available.

Figure 4B:
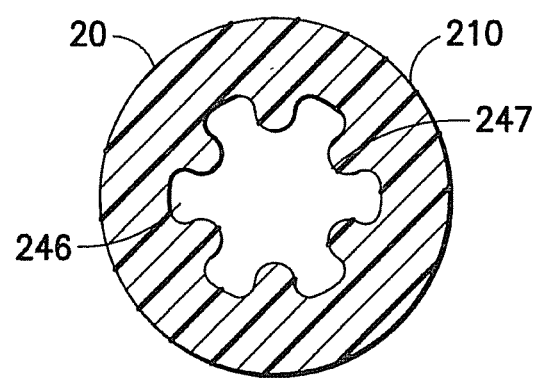

As shown in FIGS. 3, 4B, and 6, fourth sidewall surface 246 of internal cavity 240 includes a plurality of internal ribs 247 extending upward along the fourth sidewall surface 246 from the rounded bottom 242 of the cavity 240 to a point intermediate along the fourth sidewall surface 246. Preferably five or six internal ribs 247 are provided within the internal cavity 240, though any suitable number may be provided. Ribs 247 have an angled surface or, in particular embodiments, a rounded surface 2471 so as to present a minimum number of sharp edges within the internal cavity 240 and minimize surface tension with the blood or specimen sample contained within the internal cavity 240 and promote the smooth flow of blood or specimen into and out of the internal cavity 240. A top surface 2472 of the internal ribs 247 is preferably beveled outward and upward from the fourth sidewall surface 246 for engagement with a stopper 320 of cap assembly 30 (shown in FIGS. 8 and 9) as will be described below. Internal ribs 247 serve to increase the surface area of internal cavity 240, which promotes mixing of the blood or specimen sample with the additive contained in the collection tube 20 and aids in the capillary flow of blood or specimen sample into and out of the internal cavity 240 during collection and transfer of the blood or specimen sample. Ribs 247 also allow for a taller internal cavity 240, as discussed above, since the ribs 247 occupy a portion of the volume of the internal cavity 240.

As shown in FIGS. 3 and 6, internal cavity 240 includes a first sidewall surface 243 tapering inwardly from the lip portion 230 and opening 241; a second, relatively short sidewall surface 244 tapering inwardly at a much less steep angle from first sidewall surface 243; a third, also relatively short, sidewall surface 245 tapering inwardly at a steeper angle from second sidewall surface 244; and a fourth sidewall surface 246 tapering inwardly from the third sidewall surface 245 and meeting a rounded bottom 242. Fourth sidewall surface 246 defines the main collection area of internal cavity 240. As previously discussed, the sidewall surfaces 243, 244, 245, and 246 cooperate to define the internal cavity 240 with a funnel shape, which promotes the free flow of blood or specimen into and out of the collection tube 20. Also, a plurality of flow directional features 248 may be provided in the internal cavity 240 between the third and fourth sidewall surfaces 245, 246. Flow directional features include a plurality of channels that promote capillary flow into the internal cavity 240 at the point of collection, i.e., the funnel area defined by the third and fourth sidewall surfaces 245, 246. Clusters of one or more channels 248 may be provided at varying intervals, such as a 180° interval, around the perimeter of the internal cavity 240 or channels 248 may be provided around the entire perimeter of the internal cavity 240. The flow directional features 248 further promote capillary flow of the blood or specimen into the internal cavity 240 and allow for directional flow through any additives sprayed into the internal cavity. Such channels 248 may also be provided at a location between two separate ribs 247, further promoting flow along the wall surface between ribs 247.

Figure 4C:
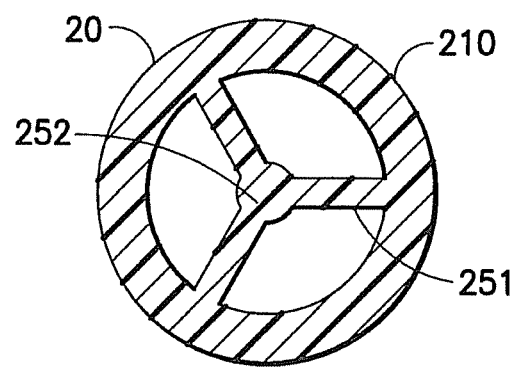
Figure 5:
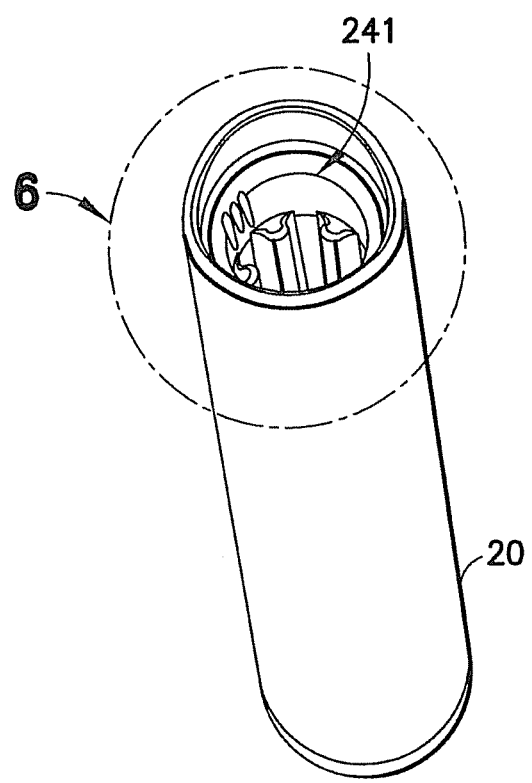
FIG. 5 is an elevated perspective view of the collection tube shown in FIGS. 1 and 2.

As shown in FIGS. 3 and 4C, the lower portion 250 of the collection tube 20 includes a generally hollow or "false" bottom defined by three structural ribs 251 extending from a central hub 252 outward to the exterior sidewall 210 of the collection tube 20. The bottoms of the structural ribs 251 extend past the bottom of the exterior sidewall 210 of the collection tube 20 and are curved so as to define the rounded bottom 253 of the collection tube 20. The "false" bottom configuration of the lower portion 250 of the collection tube 20 assists in injection molding of the collection tube 20 by promoting plastic flow. Formation of a rounded bottom 253 provides compatibility with standard medical testing instruments.

Figure 7:
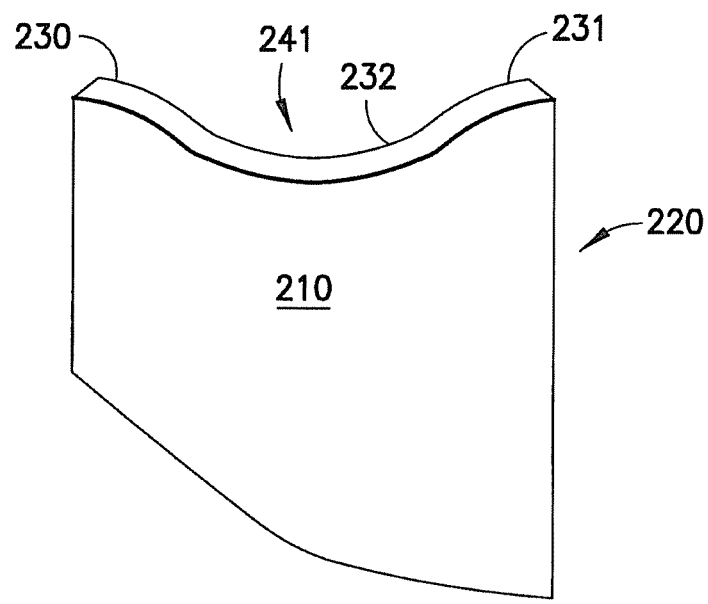
FIG. 7 is a detailed side view of the upper portion of the collection tube shown in FIGS. 1 and 2.

As shown in FIGS. 3, 6, and 7, the collection tube 20 includes a lip portion 230 at the top end of the collection tube 20, which surrounds the top opening 241 of the internal cavity 240. Lip portion 230 is a dual lip suitable for capillary collection. The dual lip includes two opposing high portions 231 and two opposing low portions 232. High portion 231 and low portion 232 of the lip portion 230 alternate around the circumference of the top opening 241. The dual lip feature 230 allows for flexibility in collection techniques and is particularly suitable for collecting capillary blood from a patient's finger. Particularly, the dual lip feature 230 is contoured to engage the skin surface of a finger at a location where capillary blood samples are taken, usually at the tip of the finger. The contour of the dual lip feature 230 minimizes scraping of the skin surface even when the lip portion 230 is pressed into or rubbed against the skin so as to prevent a capillary blood sample from being contaminated by skin particles that have been scraped away from the skin surface.

Figure 8:
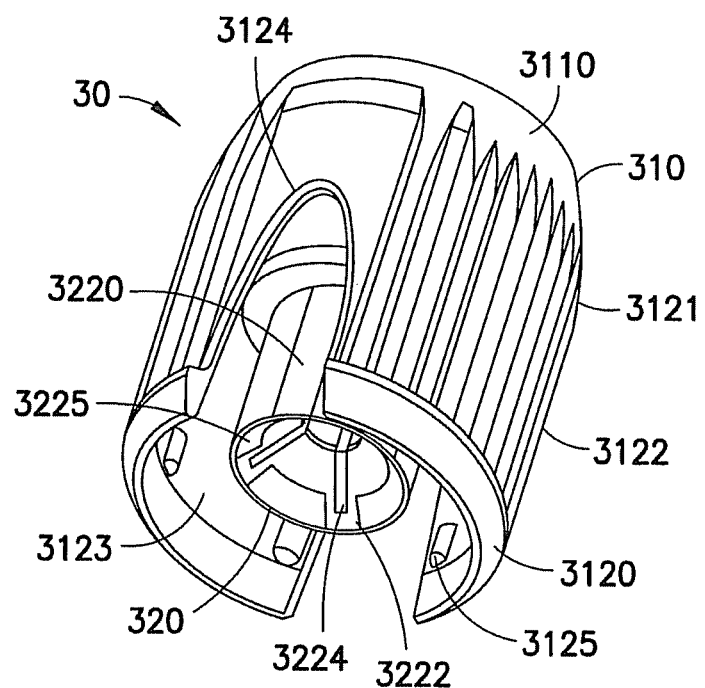
FIG. 8 is a lowered perspective view of the cap assembly shown in FIGS. 1 and 2.
Figure 9:
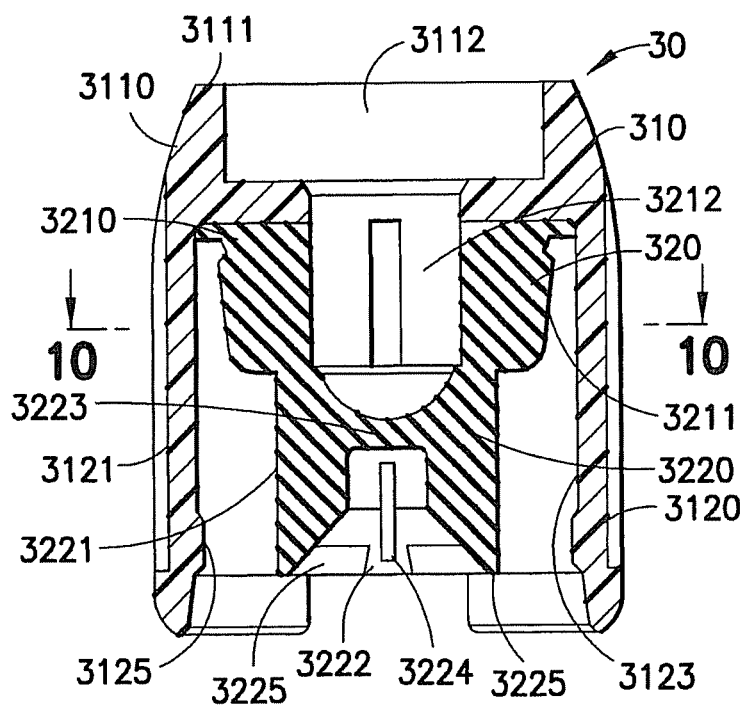
FIG. 9 is a vertical cross-sectional view of the cap assembly shown in FIG. 8.
Figure 10:
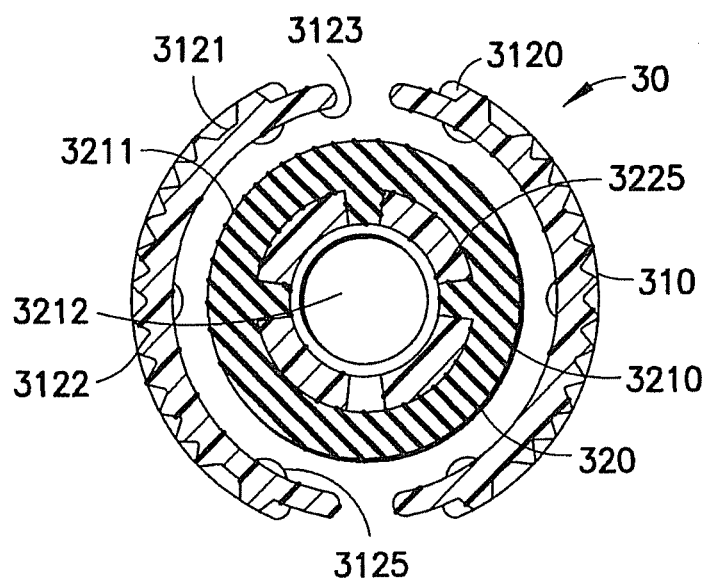
FIG. 10 is a horizontal cross-sectional view of the cap assembly taken along line 10-10, shown in FIG. 9.
Figure 11:
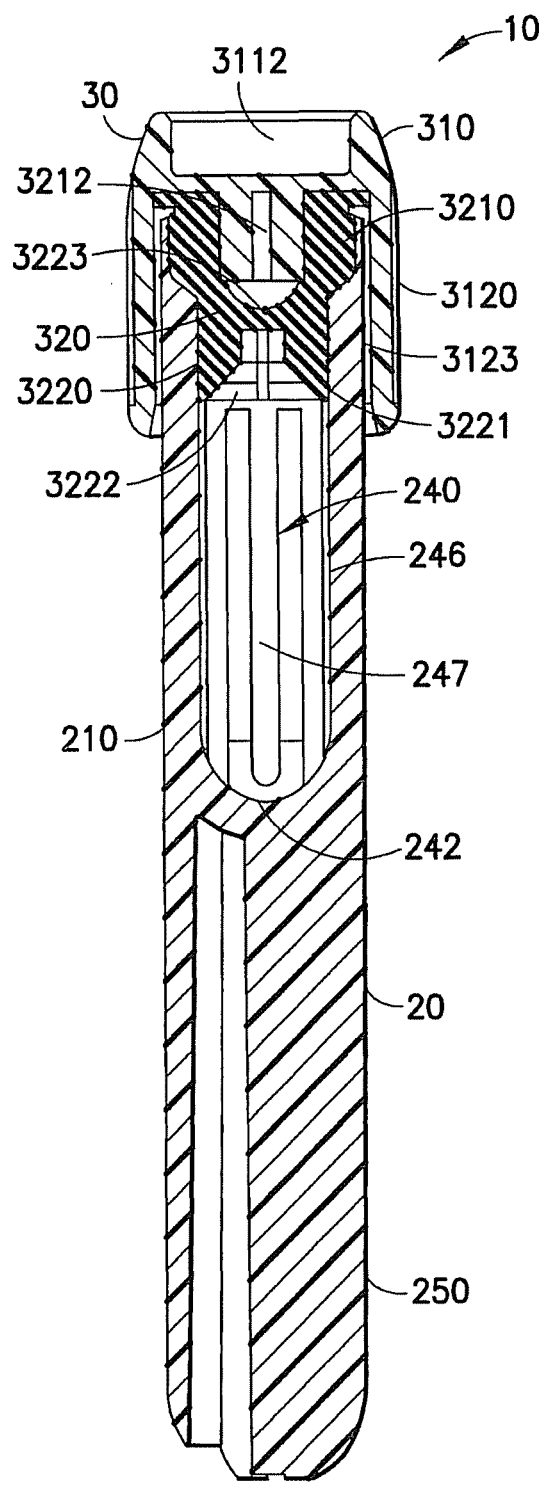
FIG. 11 is a vertical cross-sectional view of the device for capillary collection of blood samples shown in FIG. 1 with the cap assembly disposed on the collection tube.

With reference to FIGS. 8-10, a cap assembly 30 is provided for covering the top opening 241 of the collection tube 20 and sealing the internal cavity 240. As shown in FIGS. 8 and 9, cap assembly 30 includes an outer cap 310 having a top covering portion 3110 and an annular skirt portion 3120 depending from the top covering portion 3110. The top covering portion 3110 defines a top surface 3111 of the outer cap 310 and includes a hole 3112 extending through the top covering portion 3110 from the top surface 3111. Annular skirt portion 3120 includes exterior surface 3121 and an interior surface 3123. Preferably, gripping features 3122 such as raised ridges or knurling are provided on the exterior surface 3121 of the annular skirt portion 3120 to assist in placement and removal of the cap assembly 30 on the collection tube 20. Protrusions 3125 are provided on the interior surface 3123 of the annular skirt portion 3120 for frictionally engaging the exterior sidewall surface 210 of the collection tube 20 when the outer cap 310 is disposed over the collection tube 20 so as to retain the cap assembly 30 in place, as shown in FIG. 11. Optionally, an annular ring may be provided on the exterior sidewall surface 210 of the collection tube 20 to provide a snap fit or interference fit between the outer cap 310 and the collection tube 30 that reduces clearance and provides tactile feedback to the medical professional or diagnostician that the cap assembly 30 has been properly fitted onto the collection tube 20.

Further, as shown in FIGS. 8 and 10, an elliptical-shaped cut out portion 3124 is provided in the annular skirt portion 3120, which assist in removal of the cap assembly 30 from the collection tube 20 and allow for visual verification of the connection between the cap assembly 30 and the collection tube 20 to ensure that the cap assembly 30 is properly secured to the collection tube 20. Alternatively, in certain configurations the elliptical-shaped cut out portion 3124 provides visualization to a medical practitioner of a probe assembly accessing an interior of the collection tube 20 as disclosed herein.

As shown in FIGS. 8 and 9, interior surface 3123 of annular skirt portion 3120 of outer cap 30 defines an internal cavity within the outer cap 30. A stopper 320 is disposed within the internal cavity. According to the current embodiment, stopper 320 and outer cap 310 are integrally molded in a two-step molding process. Preferably, outer cap 310 is formed from a hard plastic or composite material while stopper 320 is formed from a soft plastic or elastomeric material so as to render the stopper pierceable and eliminate air bubbles in the hematology instrument. Further, as shown in FIGS. 8-10, stopper 320 includes hard plastic inserts 3225 alternating with the soft plastic or elastomeric material of the stopper 320. The hard plastic inserts 3225 assist in the two-step molding process by providing a larger surface area for the bond between the stopper 320 and the outer cap 310.

Stopper 320 includes an upper portion 3210 and a lower portion 3220. Upper portion 3210 has an exterior surface 3211 and a recess 3212 defined therein. The recess 3212 is in communication with the hole 3112 defined in the upper portion 3110 of the outer cap 310 and may be partially defined by the lower portion 3220 of the stopper 320. Lower portion 3220 has an exterior surface 3221 and a funnel-shaped recess 3222 defined therein. Funnel-shaped recess 3222 extends upward into the lower portion 3220 from the bottom surface 3226 of the stopper 320. The funnel-shaped recess 3222 and the recess 3212 defined in the upper portion 3210 of the stopper 320 are separated by a pierceable closure 3223. Pierceable closure 3223 is preferably formed of a soft plastic or elastomeric material that is easily pierceable by a standard probe needle 420 (shown in FIG. 13) and has the ability to re-seal after the probe needle 420 is removed from the stopper 320. Preferably, funnel-shaped recess 3222 includes a plurality of capillary channels 3224 defined within the lower portion 3220 of the stopper 320. Capillary channels 3224 are provided at equal intervals around the circumference of the funnel-shaped recess 3222 and are provided to break the surface tension and enhance the capillary flow of a blood or specimen sample being transferred from the internal cavity 240 of the collection tube 20 to a probe assembly 40 (shown in FIGS. 12 and 13) of a testing instrument.

As shown in FIGS. 9 and 10, the exterior surface 3211 of the upper portion 3210 of the stopper 320 is of a generally cylindrical cross-sectional shape having an inwardly tapering diameter from the top to the bottom of the upper portion 3210 of the stopper 320. Exterior surface 3221 of lower portion 3220 of stopper 320 is of a cylindrical cross-sectional shape having a constant diameter.

Referring to FIG. 11, a cross-sectional view of the device 10 with the cap assembly 30 disposed on the collection tube 20 is shown. As shown, cap assembly 30 is disposed on the collection tube 20 such that top portion 3110 of the outer cap 310 is disposed over the top opening 210 of the collection tube 20 and the annular skirt portion 3120 of the outer cap 310 substantially surrounds a portion of the exterior sidewall surface 210 of the collection tube 20 and engages the exterior sidewall surface 210 with protrusions 3125.

The upper portion 3210 of the stopper 320 rests on top of the opposing high portions 231 of the lip portion 230 and extends into the top opening 241 of the collection tube 20 and engages the first and second sidewall surfaces 243, 244 of the internal cavity 240 so as to seal the internal cavity 240 of the collection tube 20. Lower portion 3220 of the stopper 320 depends further into the internal cavity 240 so as to engage the fourth sidewall surface 246 of the internal cavity 240. Bottom surface 3226 of the stopper 320 is disposed between the beveled top surfaces 2472 of the internal ribs 247 and the fourth sidewall surface 246 such that the funnel-shaped recess 3222 is in communication with the internal cavity 240 and the beveled top surfaces 2472 of the internal ribs 247 engage the funnel-shaped recess 3222.

The device 10 for capillary collection of blood samples or other biological specimens is used as follows. After the skin surface of a patient is pierced according to known techniques, a blood sample is drawn from the pierced capillary located just beneath the skin surface. Collection tube 20 is then placed near the location of the piercing such that the lip portion 230 of the collection tube 20 engages the skin surface. Blood or specimen is then allowed to flow into the internal cavity 240 of the collection tube 20 via the top opening 241. Top opening 241 is suitably large so as to ease collection of the blood or specimen sample.

As discussed above, internal cavity 240 has a generally tapered and rounded profile so as to channel the flow of blood or specimen from the top opening 241 into the internal cavity 240. Flow directional features 248 disposed in the third and fourth sidewall surfaces 245, 246 of the internal cavity promote capillary flow of the blood or specimen further into the internal cavity 240. Internal ribs 247 further promote such capillary flow into the internal cavity 240 and increase the surface area of the internal cavity 240 so as to promote mixing between the collected blood or specimen and additives sprayed into the internal cavity 240.

After collection of the blood or specimen sample is completed, cap assembly 30 is disposed on the collection tube as described above so as to close the top opening 241 and seal the internal cavity 240 with the blood or specimen sample contained therein. Cap assembly 30 is suitably large so that it is easily removable from the collection tube 20.

It is to be appreciated that though the device 10 is described with reference to a capillary collection technique where the collection tube 20 is non-evacuated, other collection techniques are still encompassed within the scope of the present invention. For instance, the stopper 320 of cap assembly 30 is suitably large and includes a pierceable closure 3223 such that cap assembly 30 may be used with an evacuated collection tube 20 or similar collection container as the stopper 320 is capable of holding a vacuum. In this instance, the device 10 may be used with intravenous collection techniques and the like rather than capillary collection.

Figure 12:
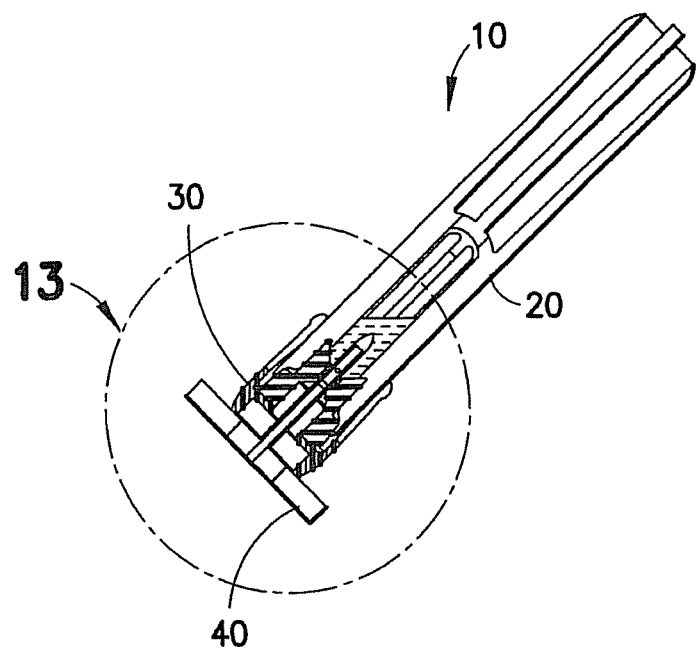
FIG. 12 is a partial cross-sectional view of the device for capillary collection of blood samples shown in FIG. 11 with the device oriented for transferring a sample to a testing device and a probe assembly inserted into the device.
Figure 13:
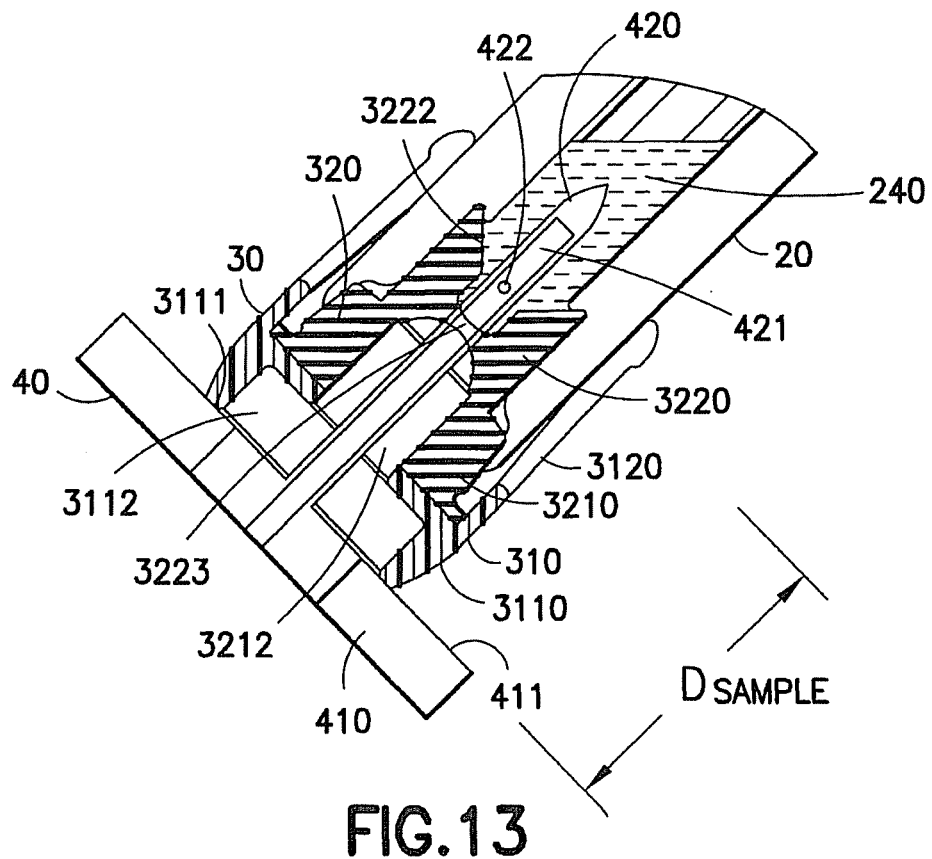
FIG. 13 is a detailed partial cross-sectional view of area "13", shown in FIG. 12.

Referring to FIGS. 12 and 13, the blood or specimen sample contained within the internal cavity 240 of the collection tube 20 is transferred to the testing instrument, such as a hematology instrument, via a probe assembly 40. As noted above, device 10 is compatible with standard testing instruments such that the device can be connected to the testing instrument via automated assembly features of the testing instrument. As shown in FIGS. 12 and 13, during automated or manual assembly, the device 10 is inverted at a 45° angle. A probe needle 420 having an internal cannula 421 and an aspiration hole 422 is then inserted into the internal cavity 240 of the collection tube 20.

As shown in FIG. 13, when inserted the probe needle 420 extends through the hole 3212 in the outer cap 310 of the cap assembly 30 and the recess 3212 in the upper portion 3210 of the stopper 320 such that it pierces the pierceable closure 3223 in the stopper 320. Device 10 is positioned on probe assembly 40 such that a contact surface 411 of the base portion 410 of probe assembly 40 engages the top surface 3111 of the outer cap 310. Preferably, upon completion of assembly, the aspiration hole 422 of the probe needle 420 is positioned within the funnel-shaped recess 3222 of the stopper 320 such that the aspiration hole 422 is in communication with the apex of the funnel-shaped recess 3222 and internal cavity 240 at a sampling distance $D_{sample}$. In one embodiment, the sampling distance $D_{sample}$ is from about 0.58 to about 0.60 inches.

Due to the inverted position of the collection tube 20 and stopper 320, the blood or specimen sample contained within the internal cavity 240 will flow downward toward the aspiration hole 422. Internal ribs 247 disposed on the fourth sidewall surface 246 of the internal cavity 240 assist in the downward flow of the sample by promoting capillary flow along the fourth sidewall surface 246 and channeling the blood or specimen sample onto the funnel-shaped recess 3222 of the stopper.

Preferably, the funnel-shaped recess 3222 of the stopper 320 is formed at a 45° angle to promote funneling of the blood or specimen sample from the fourth sidewall surface 246 and internal ribs 247 toward the aspiration hole 422 of the probe needle 420. Also, the angle of the funnel-shaped recess 3222 helps to push up dead volume in the flow of blood or specimen sample toward the aspiration hole 422. Capillary channels 3224 in the funnel-shaped recess 3222 (shown in FIGS. 8 and 9) further promote capillary flow of blood or specimen sample along the funnel-shaped recess 3222 toward the aspiration hole 422. Thus, funnel-shaped recess 3222 of stopper 320 acts as a space elimination feature within the stopper 320, which positions the blood or specimen sample at the aspiration hole 422 of the probe needle 420. The space elimination feature of the funnel-shaped recess 3222 thus operates to maximize the low volume of blood or specimen sample contained within the internal cavity 240 of the collection tube 20 and avoid waste or non-utilization of collected blood or specimen samples.

It is to be appreciated, then, that the current invention according to the first embodiment described above presents significant advantages over conventional microtubes or collection containers and cap assemblies. Specifically, collection tube 20 contains an internal cavity 240 shaped to promote the efficient flow of blood or specimen sample into and out of the cavity 240 such that a minimal amount of blood or specimen sample is wasted during collection and transfer to a testing instrument. Also, a dual lip feature 230 contoured to engage the skin surface of a patient, especially at the top of the finger, and wide top opening 241 are provided on an upper portion 220 of the collection tube 20 in order to ease collection of a drawn sample and minimize contamination of the sample during collection. Further, stopper 320 of cap assembly 30 is provided with a funnel-shaped or conical recess 3222, which funnels blood or specimen sample toward the probe assembly 40 during transfer of the blood or specimen sample to a testing instrument. Thus the device 10 according to the first embodiment of the present invention eliminates the known dead volume of conventional microtube assemblies such that less blood or specimen sample is required to be collected and more tests can be performed on a lower volume of blood or specimen sample.

Figure 14:
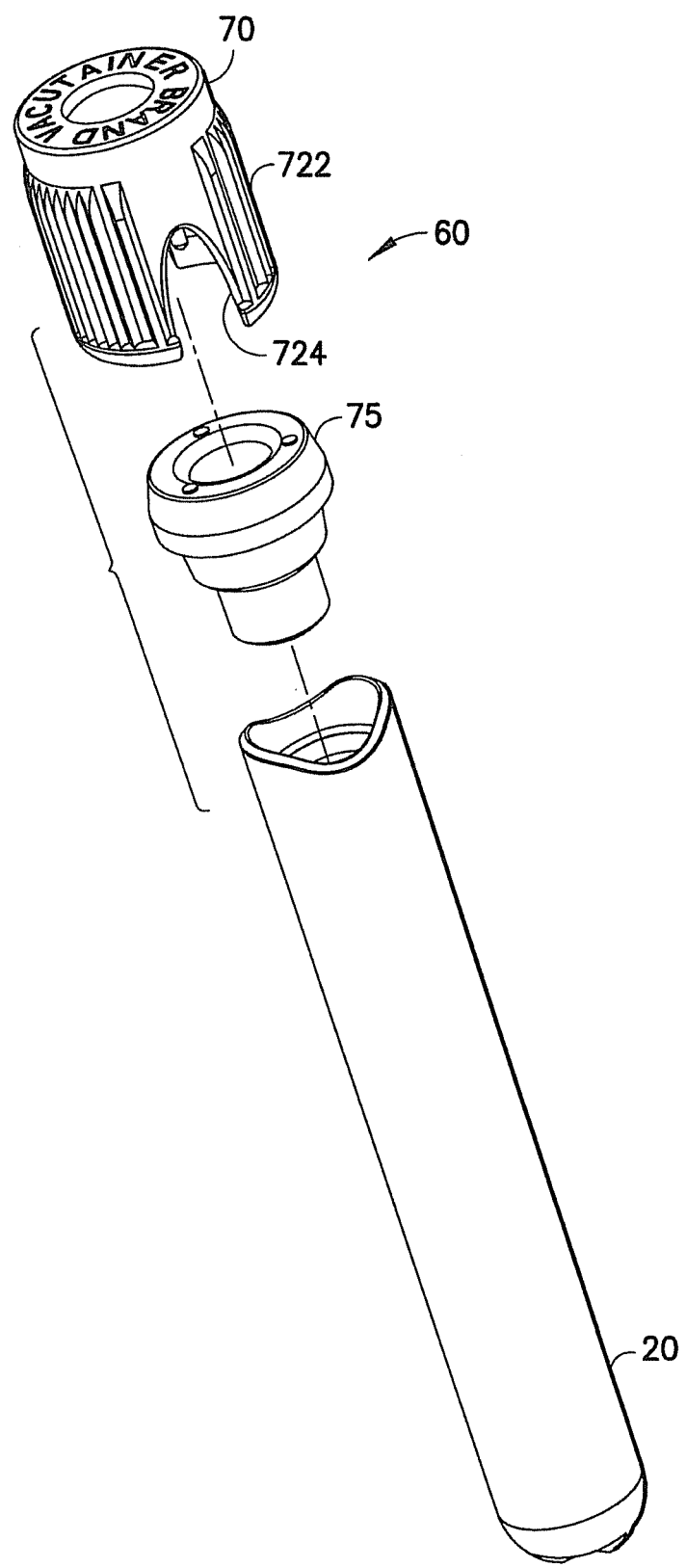
FIG. 14 is an exploded perspective view of a device for capillary collection of blood samples pursuant to a second embodiment of the present invention.

Referring to FIG. 14, a collection device 60 according to a second embodiment of the present invention is shown. Collection device 60 includes a collection tube 20 for the collection, storage, and eventual transfer of biological specimens, including blood samples, for purposes of diagnostic testing. A molded cap 70 and stopper 75 are disposed on the collection tube 20 so as to cover and seal the collection tube 20 and any sample contained therein. According to the embodiment shown, molded cap 70 and stopper 75 are removably disposed and attached to the collection tube 20 after collection of the sample contained therein. It is to be understood that the device 60 according to the second embodiment is largely similar to the device 10, according to the first embodiment discussed above, in terms of use and operability and utilizes the same collection tube 20 as the device 10, according to the first embodiment. In contrast to the device 10, device 60, according to the second embodiment, utilizes a molded cap 70 and stopper 75 formed as separate pieces rather than being integrally molded.

With reference to FIGS. 15-17, a molded cap 70 and stopper 75 are provided for covering the top opening 241 of the collection tube 20 and sealing the internal cavity 240. As shown in FIG. 16, molded cap 70 has a top covering portion 710 and an annular skirt portion 720 depending from the top covering portion 710. The top covering portion 710 defines a top surface 711 of the molded cap 710 and includes a hole 712 extending through the top covering portion 710 from the top surface 711. Annular skirt portion 720 includes a straight-walled exterior surface 721 and an interior surface 723. Preferably, gripping features 722 (shown in FIG. 14) such as raised ridges or knurling are provided on the exterior surface 721 of the annular skirt portion 720 to assist in placement and removal of the molded cap 70 and stopper 75 on the collection tube 20. Protrusions 725 are provided on the interior surface 723 of the annular skirt portion 720 for frictionally engaging the exterior sidewall surface 210 of the collection tube when the molded cap 70 is disposed over the collection tube 20 so as to retain the molded cap 70 and stopper 75 in place. Also, an annular ring 726 is provided on the interior surface 723 of the annular skirt portion 720 to further reduce clearance between the molded cap 70 and the exterior sidewall surface 210 of the collection tube.

Further, as shown in FIGS. 14 and 15, elliptical-shaped cut outs 724 are provided in the annular skirt portion 720, which assist in removal of the molded cap 70 and stopper 75 from the collection tube 20 and allow for visual verification of the connection between the molded cap 70 and stopper 75 and the collection tube 20 to ensure that the molded cap 70 and stopper 75 are properly secured to the collection tube 20.

As shown in FIGS. 15 and 16, interior surface 723 of annular skirt portion 720 of molded cap 70 defines an internal cavity 727 within the molded cap 70. A stopper 75 is disposed within the internal cavity 727. According to the current embodiment, stopper 75 is press fit into the molded cap 70 by lubing the stopper 75 and then pressing the molded cap 70 over the stopper 75. The assembled molded cap 70 and stopper 75 are then disposed on the collection tube 20, as discussed above with respect to the first embodiment. Preferably, outer cap 70 is formed from a hard plastic or composite material while stopper 75 is formed from a soft plastic or elastomeric material so as to render the stopper pierceable and eliminate air bubbles in the hematology instrument.

As shown in FIGS. 15 and 17, stopper 75 includes an upper portion 750 and a lower portion 760. Upper portion 750 has an exterior mating surface 751, an exterior sealing surface 753, and a recess 752 defined therein. The recess 752 is in communication with the hole 712 defined in the upper portion 710 of the molded cap 70 when the stopper 75 is fitted in the molded cap 70 and may be partially defined by the lower portion 760 of the stopper 75. Lower portion 760 has an exterior surface 761 and a funnel-shaped recess 762 defined therein. Funnel-shaped recess 762 extends upward into the lower portion 760 from the bottom surface 764 of the stopper 320. The funnel-shaped recess 762 and the recess 752 defined in the upper portion 750 of the stopper 75 are separated by a pierceable closure 763. Pierceable closure 763 is preferably formed of a soft plastic or elastomeric material that is easily pierceable by a standard probe needle 420 (shown in FIG. 13) and has the ability to re-seal after the probe needle 420 is removed from the stopper 75. Funnel-shaped recess 762 may also include a plurality of capillary channels defined within the lower portion of the stopper 75, as described above with respect to the first embodiment.

As shown in FIGS. 15 and 17, the exterior mating surface 751 of the upper portion 750 of the stopper 75 is of a generally cylindrical cross-sectional shape having an outwardly tapering diameter from the top of the upper portion 750 of the stopper 75. Exterior mating surface 751 is suitably large in diameter so as to frictionally engage the interior surface 723 of the annular skirt portion 720 of molded cap 70 via an interference fit when the molded cap 70 is pressed on to the stopper 75. Exterior sealing surface 753 of the upper portion 750 of stopper 75 is also of a generally cross-sectional shape having an inwardly tapering diameter toward the lower portion 760 of the stopper 75. Exterior surface 761 of lower portion 760 of stopper 75 is of a cylindrical cross-sectional shape having a constant diameter.

Molded cap 70 and stopper 75, after being assembled together, are disposed on collection tube 20 in the same manner as cap assembly 30 of the first embodiment is disposed on the collection tube 20, as shown in FIG. 11. Molded cap 70 and stopper 75 are disposed on the collection tube 20 such that top portion 710 of the molded cap 70 is disposed over the top opening 210 of the collection tube 20 and the annular skirt portion 720 of the molded cap 70 substantially surrounds a portion of the exterior sidewall surface 210 of the collection tube 20 and engages the exterior sidewall surface 210 with protrusions 725 and annular ring 726.

The upper portion 750 of the stopper 75 rests on top of the opposing high portions 231 of the lip portion 230 and extends into the top opening 241 of the collection tube 20 such that the exterior sealing surface 753 engages the first and second sidewall surfaces 243, 244 of the internal cavity 240 so as to seal the internal cavity 240 of the collection tube 20. Lower portion 760 of the stopper 75 depends further into the internal cavity 240 so as to engage the fourth sidewall surface 246 of the internal cavity 240. Bottom surface 764 of the stopper 75 is disposed between the beveled top surfaces 2472 of the internal ribs 247 and the fourth sidewall surface 246 such that the funnel-shaped recess 262 is in communication with the internal cavity 240 and the beveled top surfaces 2472 of the internal ribs 247 engage the funnel-shaped recess 762.

Blood or specimen sample contained within the internal cavity 240 of the collection tube 20 is transferred to a testing instrument via a probe assembly in the same manner as discussed above with respect to the first embodiment and as shown in FIGS. 12 and 13. When inserted, the probe needle 420 extends through the hole 712 in the molded cap 70 and the recess 752 in the upper portion 750 of the stopper 75 such that it pierces the pierceable closure 763 in the stopper 75. Device 60 is positioned on probe assembly 40 such that a contact surface 411 of base portion 410 of the probe assembly 40 engages the top surface 711 of the molded cap 70. Preferably, upon completion of assembly, the aspiration hole 422 of the probe needle 420 is positioned within the funnel-shaped recess 762 of the stopper 75 such that the aspiration hole 422 is in communication with the funnel-shaped recess 762 and internal cavity 240.

Figure 18:
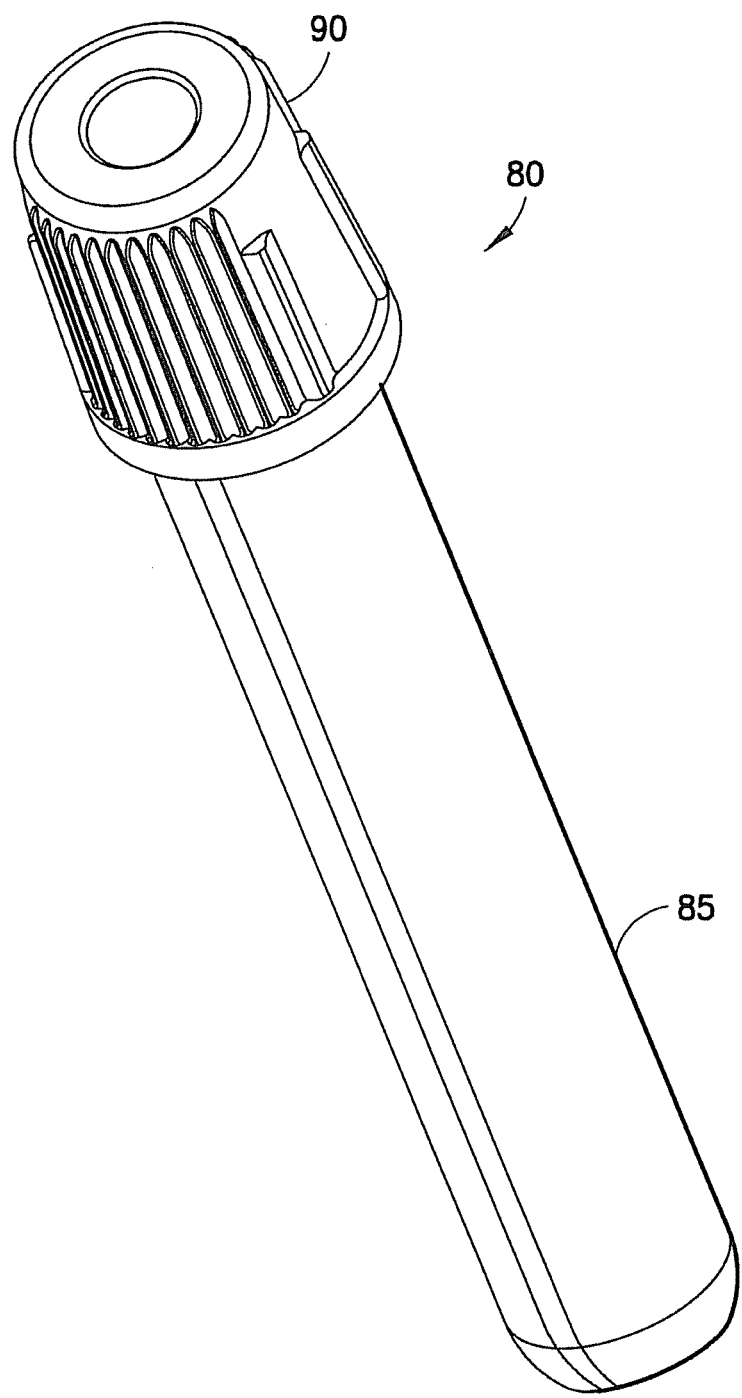
FIG. 18 is a perspective view of a device for capillary collection of blood samples pursuant to a third embodiment of the present invention.
Figure 19:
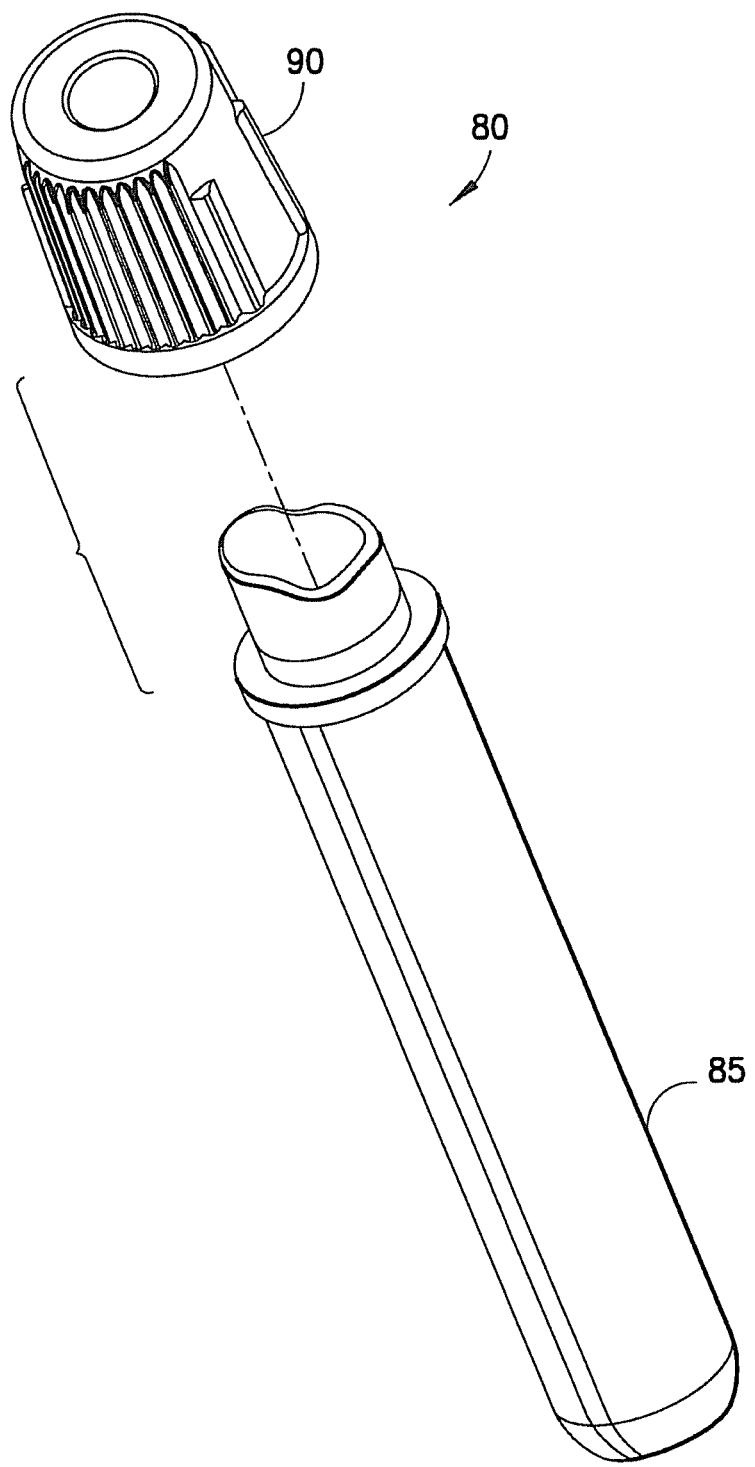
FIG. 19 is an exploded perspective view of the capillary collection device shown in FIG. 18.

Referring to FIGS. 18 and 19, a collection device 80 according to a third embodiment of the present invention is shown. Collection device 80 includes a collection tube 85 for the collection, storage, and eventual transfer of biological specimens, including blood samples, for purposes of diagnostic testing. A cap assembly 90 is disposed on the collection tube 85 so as to cover and seal the collection tube 85 and any sample contained therein. According to the embodiment shown, cap assembly 90 is removably disposed and attached to the collection tube 85 after collection of the sample contained therein.

Figure 20:
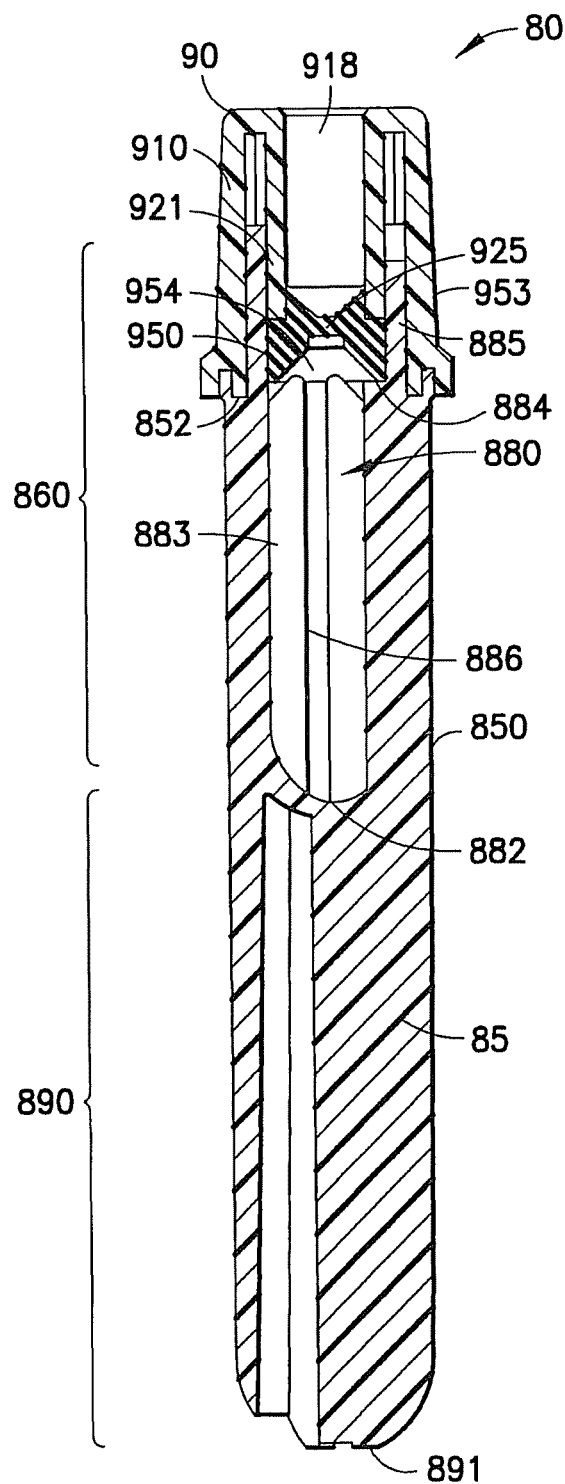
FIG. 20 is a vertical cross-sectional view of the device for capillary collection of blood samples shown in FIG. 18.
Figure 23:
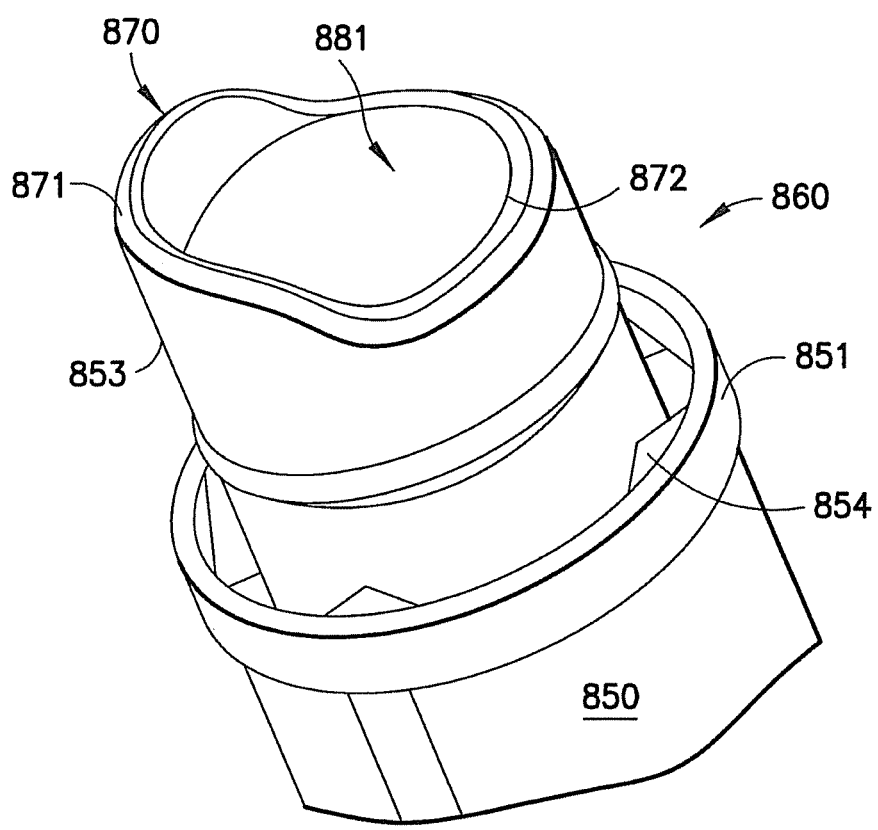
FIG. 23 is a detailed perspective view of the top area of the collection tube shown in FIG. 19.

As shown in FIGS. 20 and 23, collection tube 85 is a microtube suited for capillary collection of blood samples having exterior dimensions of 13×75 mm so as to be compatible with standard testing instruments. Collection tube 85 is injection molded from suitable plastic or composite material as is known to be suitable by those of ordinary skill in the art. It is also contemplated herein that although the collection tube 85 is shown herein as a single piece tube, a double walled configuration or a collection container having an insert may be contemplated with the present invention. Collection tube 85 is defined by an exterior sidewall 850 extending from a rounded tube bottom 891 to a lip portion 870. Collection tube 85 includes upper and lower portions 860, 890. Lower portion 890 of the collection tube 85 may include a hollow or "false" bottom as discussed above with respect to the collection tube 20 according to the first and second embodiments.

Upper portion 860 of collection tube 85 defines an internal cavity 880 for the collection, containment, and eventual transfer of biological specimens. Internal cavity 880 extends through the upper portion 860 of the collection tube 85 from a rounded bottom 882 to a top opening 881 in the collection tube 85. Internal cavity 880 of collection tube 85 may be coated with an additive sprayed into the collection tube 85 for preserving a blood or specimen sample contained within the collection tube 85 during storage or for other diagnostic purposes as is known by those of ordinary skill in the art. As shown in FIG. 23, the top opening 881 is surrounded by lip portion 870.

With reference to FIG. 20, internal cavity 880 is defined within the upper portion 860 of the collection tube 85 by two of sidewall surfaces 883 and 885. A second sidewall surface 885 of internal cavity 880 defines a smooth, cylindrical surface so as to promote the unobstructed flow of specimen from the top opening 881 further into the internal cavity 880.

As shown in FIG. 20, a first sidewall surface 883 of internal cavity 880 includes a plurality of internal ribs 886 extending upward along the first sidewall surface 883 from the rounded bottom 882 of the cavity 880 to the second sidewall surface 885. Preferably five or six internal ribs 886 are provided within the internal cavity 880, though any suitable number may be provided. A top surface 884 of the internal ribs 886 is preferably beveled outward and upward from the first sidewall surface 883 for engagement with a stopper 950 of cap assembly 90 (shown in FIGS. 20 and 25) as will be described below. Internal ribs 886 serve to increase the surface area of internal cavity 880, which promotes mixing of the blood or specimen sample with the additive contained in the collection tube 85 and aids in the capillary flow of blood or specimen sample into and out of the internal cavity 880 during collection and transfer of the blood or specimen sample. Ribs 886 also allow for a taller internal cavity 880, as discussed above, since the ribs 886 occupy a portion of the volume of the internal cavity 880.

As shown in FIGS. 20 and 23, the collection tube 85 includes a lip portion 870 at the top end of the collection tube 85, which surrounds the top opening 881 of the internal cavity 880. Lip portion 870 includes a flat portion 872 and a curved receiving portion 871 extending upward from the flat portion 872. The curved receiving portion 871 may extend from the flat lip portion 872 to any suitable height. The curved receiving portion 871 may have any suitable curvature, such as corresponding to the curvature of the flat lip portion 872, or having a lesser or greater curvature as desired.

As shown in FIGS. 20 and 23, a seating flange having a bottom surface 852 and an upraised surface 851 extending from the bottom surface 852 may be positioned about the exterior sidewall 850 of the collection tube 85 proximate to the lip portion 870 and top opening 881. The seating flange defines an internal trough between the upraised surface 851 of the seating flange and a top portion 853 of the exterior sidewall 850 of the collection tube 85. A plurality of lugs 854 is disposed on the upraised surface 851 within the internal trough. Lugs 854 may be of any suitable shape, including a generally triangular shape, as shown in FIG. 23, and may each include cam surfaces.

Figure 24:
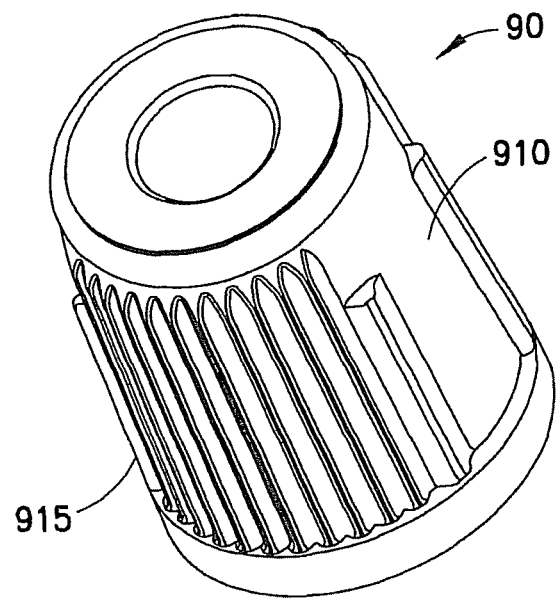
FIG. 24 is an elevated perspective view of the cap assembly shown in FIGS. 18 and 19.
Figure 25:
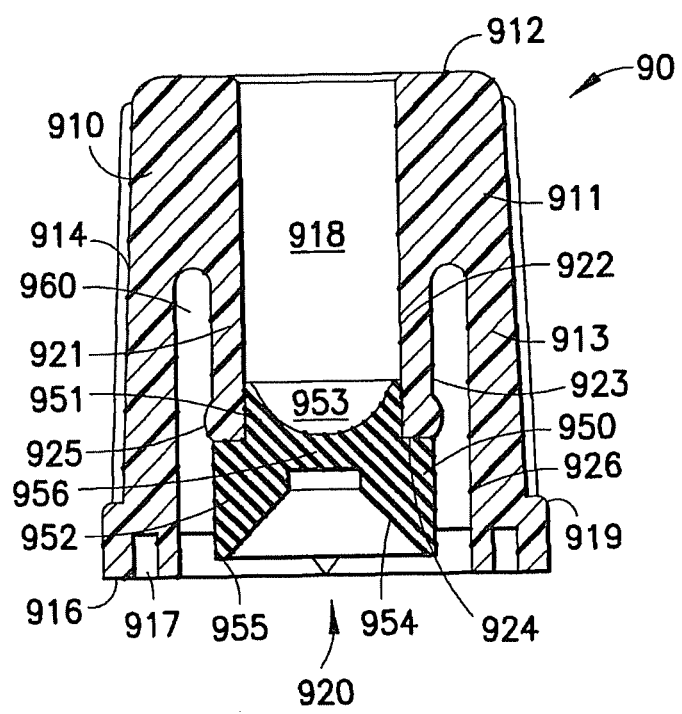
FIG. 25 is a vertical cross-sectional view of the cap assembly shown in FIG. 24.

With reference to FIGS. 18-20, 24, and 25, a cap assembly 90 is provided for covering the top opening 881 of the collection tube 85 and sealing the internal cavity 885. As shown in FIGS. 20, 24, and 25, cap assembly 90 includes an outer cap 910 having a ring-shaped top covering portion 911 and an external annular skirt portion 913 depending from the top covering portion 911. The top covering portion 911 defines a top surface 912 of the outer cap 910 and includes an interior cavity 918 extending through the top covering portion 911 from the top surface 912 to a bottom opening 920 in the outer cap 910. External annular skirt portion 913 and top covering portion 911 define an exterior surface 914 of the cap assembly 90. Preferably, gripping features 915 such as raised ridges or knurling are provided on the exterior surface 914 to assist in placement and removal of the cap assembly 90 on the collection tube 85. External annular skirt portion 913 has a bottom surface 916 having a recess 917 defined therein so as to create a bottom stop ledge for the outer cap 910. A plurality of protrusions 926 are provided on the interior surface 919 of the external annular skirt portion 913 for frictionally engaging the exterior sidewall surface 850 of the collection tube 85 when the outer cap 910 is disposed over the collection tube 85 so as to retain the cap assembly 90 in place on the collection tube 85.

Outer cap 910 also includes an internal annular skirt portion 921 depending from the top covering portion 911 and into the cavity 918 such that the internal annular skirt portion 921 is partially co-extensive with the external annular skirt portion 913. Internal annular skirt portion 921 has an interior surface 922 having the same diameter as the cavity 918 through the top covering portion 911 so as to form a continuous surface from the bottom surface 924 of the internal annular skirt portion 921 to the top surface 912 of the outer cap 910. Internal annular skirt portion 921 has an outer surface 923 spaced from the interior surface 919 of the external annular skirt portion 913 so as to form a channel 960 within the internal cavity 918 of the outer cap 910 between the external and internal annular skirt portions 913, 921. An annular protruding ring 925 may also be provided on the outer surface 923 of the internal annular skirt portion 921 at the base thereof for frictionally engaging the second internal sidewall surface 885 of the internal cavity 880 of the collection tube 85 when the cap assembly 90 is disposed on the collection tube 85 so as to retain the cap assembly 90 in place.

As shown in FIGS. 20 and 24, a stopper 950 is disposed within the internal cavity 918 of the outer cap 910. According to the current embodiment, stopper 950 and outer cap 910 are integrally molded at the interior 922 and bottom 924 surfaces of the internal skirt portion 921 of the outer cap 910 in a two-step molding process. Preferably, outer cap 910 is formed from a hard plastic or composite material while stopper 950 is formed from a soft plastic or elastomeric material so as to render the stopper 950 pierceable and eliminate air bubbles in the hematology instrument.

Stopper 950 includes an upper portion 951 and a lower portion 952. Upper portion 951 has a recess 953 defined therein. The recess 953 is in communication with the internal cavity 918 of the outer cap 910. Lower portion 952 has a funnel-shaped recess 954 defined therein. Funnel-shaped recess 954 extends upward into the lower portion 952 from the bottom surface 955 of the stopper 950. The funnel-shaped recess 954 and the recess 953 defined in the upper portion 951 of the stopper 950 are separated by a pierceable closure 956. Pierceable closure 956 is preferably formed of a soft plastic or elastomeric material that is easily pierceable by a standard probe needle 420 (shown in FIG. 22) and has the ability to re-seal after the probe needle 420 is removed from the stopper 950.

As shown in FIGS. 20 and 25, the upper portion 951 of the stopper 950 is of a cylindrical cross-sectional shape and has a diameter corresponding to the diameter of the interior surface 922 of the inner annular skirt portion 921. The lower portion 952 of stopper 950 is of a cylindrical cross-sectional shape and has a diameter corresponding to the diameter of the outer surface 923 of the inner annular skirt portion 921.

Referring to FIG. 20, a cross-sectional view of the device 80 with the cap assembly 90 disposed on the collection tube 85 is shown. As shown, cap assembly 90 is disposed on the collection tube 85 such that top portion 911 of the outer cap 910 is disposed over the top opening 881 of the collection tube 85 and the external annular skirt portion 913 of the outer cap 910 substantially surrounds the top portion 953 of the exterior sidewall surface 950 of the collection tube 85 and engages the top portion 953 of the exterior sidewall surface 950 with protrusions 926. A portion of the bottom surface 916 of the external annular skirt portion 913 engages the bottom surface 852 of the seating ledge on the collection tube 85 with the upraised surface 851 of the seating ledge extending into the recess 917 defined in the bottom surface. Interior surface 919 of external annular skirt portion 913 may optionally include triangle-shaped cam protrusions proximate to the bottom opening 920 for engaging the lugs 954 on the upraised surface 851 of the seating ledge in a cam arrangement such that cap assembly 90 may be unseated from the seating ledge by twisting the cap assembly 90.

The lip portion 870 as well as the upper portion 860 of the collection tube 85 are engaged by the internal and external annular skirt portions 921, 923 of the outer cap 910 such that the internal annular skirt portion 921 extends into the top opening 881 of the collection tube 85 and engages the second sidewall surface 885 of the internal cavity 880. The lower portion 952 of stopper 950 depends further into the internal cavity 880 so as to engage and seal the internal cavity 880 at the second sidewall surface 885. Bottom surface 955 of the stopper 950 is disposed between the beveled top surfaces 884 of the internal ribs 846 and the first sidewall surface 883 such that the funnel-shaped recess 954 is in communication with the internal cavity 880 and the beveled top surfaces 884 of the internal ribs 886 engage the funnel-shaped recess 854.

Figure 21:
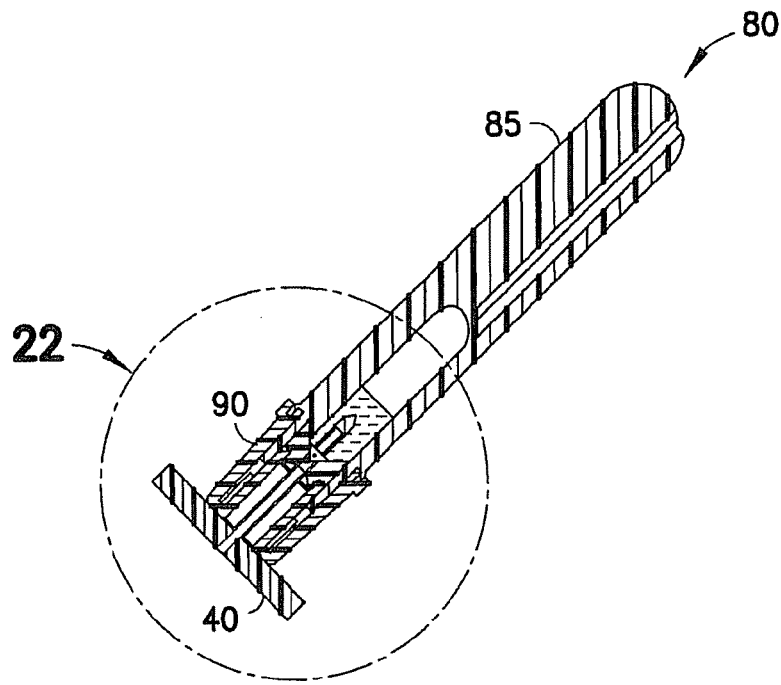
FIG. 21 is a partial cross-sectional view of the device for capillary collection of blood samples shown in FIG. 18 with the device oriented for transferring a sample to a testing device and a probe assembly inserted into the device.
Figure 22:
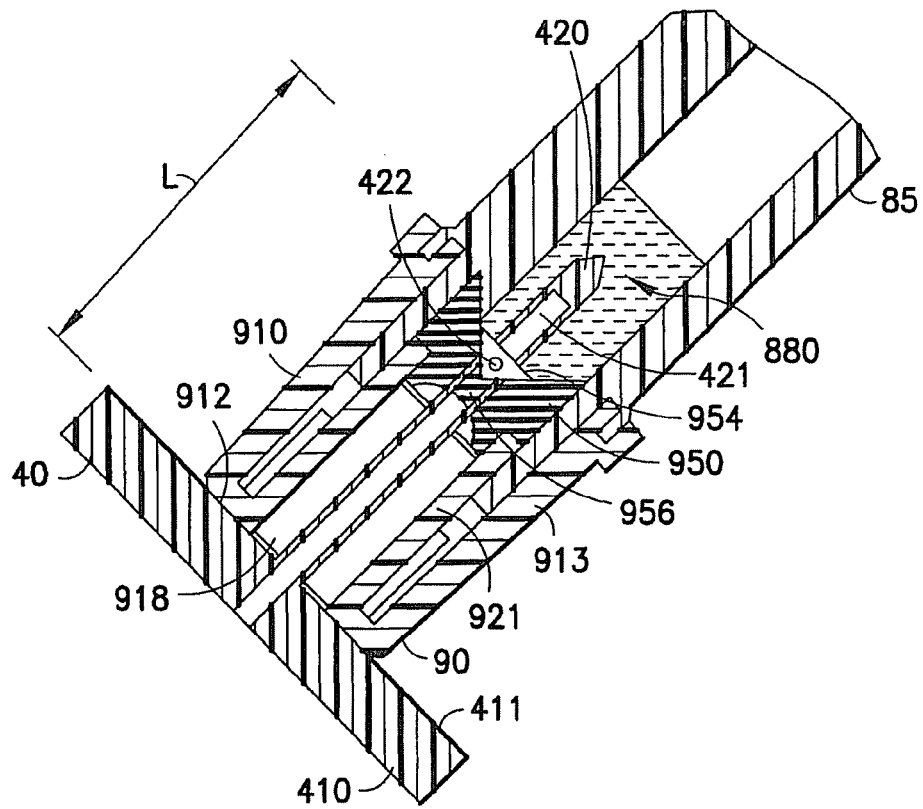
FIG. 22 is a detailed partial cross-sectional view of area "22", shown in FIG. 21.

It is to be appreciated that the device 80 described above can be used in a similar manner as described above with respect to the devices 10, 60 according to the first and second embodiments, respectively, with the blood or specimen sample being collected via the curved receiving portion 871 of the lip portion 870 of the collection tube 85. Referring to FIGS. 21 and 22, the blood or specimen sample contained within the internal cavity 880 of the collection tube 85 is transferred to the testing instrument, such as a hematology instrument, via a probe assembly 40. As noted above, device 80 is compatible with standard testing instruments such that the device can be connected to the testing instrument via automated assembly features of the testing instrument. As shown in FIGS. 21 and 22, during automated or manual assembly, the device 80 is inverted at a 45° angle. A probe needle 420 having an internal cannula 421 and an aspiration hole 422 is then inserted into the internal cavity 880 of the collection tube 85.

As shown in FIG. 22, when inserted, the probe needle 420 extends through the interior cavity 918 in the outer cap 910 of the cap assembly 90 and the recess 953 in the upper portion 951 of the stopper 950 such that it pierces the pierceable closure 956 in the stopper 950. Device 80 is positioned on probe assembly 40 such that a contact surface 411 of the base portion 410 of probe assembly 40 engages the top surface 912 of the outer cap 910. According to the present embodiment, stopper 950 is disposed on the internal annular skirt portion 921 of the outer cap 910 within the interior cavity 918 such that a fixed length L measured from the top surface 912 of the outer cap 910 to the funnel-shaped recess 954 in the lower portion 952 of the stopper 950 corresponds to the distance between the contact surface 411 of the probe assembly and the aspiration hole 422 along the probe needle 420. In this manner, the aspiration hole 422 of the probe needle 420 is positioned within the funnel-shaped recess 954 of the stopper 950 such that the aspiration hole 422 is in communication with the funnel-shaped recess 954 and internal cavity 880.

Due to the inverted position of the collection tube 85 and stopper 950, the blood or specimen sample contained within the internal cavity 880 will flow downward toward the aspiration hole 422. Internal ribs 886 disposed on the first sidewall surface 883 of the internal cavity 880 assist in the downward flow of the sample by promoting capillary flow along the first sidewall surface 883 and channeling the blood or specimen sample onto the funnel-shaped recess 954 of the stopper 950.

Preferably, the funnel-shaped recess 954 of the stopper 950 is formed at a 45° angle to promote funneling of the blood or specimen sample from the first sidewall surface 883 and internal ribs 886 toward the aspiration hole 422 of the probe needle 420. Also, the angle of the funnel-shaped recess 954 helps to push up dead volume in the flow of the blood or specimen sample toward the aspiration hole 422. Thus, funnel-shaped recess 954 of stopper 950 acts as a space elimination feature within the stopper 950, which positions the blood or specimen sample at the aspiration hole 422 of the probe needle 420. The space elimination feature of the funnel-shaped recess 954 thus operates to maximize the low volume of the blood or specimen sample contained within the internal cavity 880 of the collection tube 85 and avoid waste or non-utilization of collected blood or specimen samples.

Figure 26:
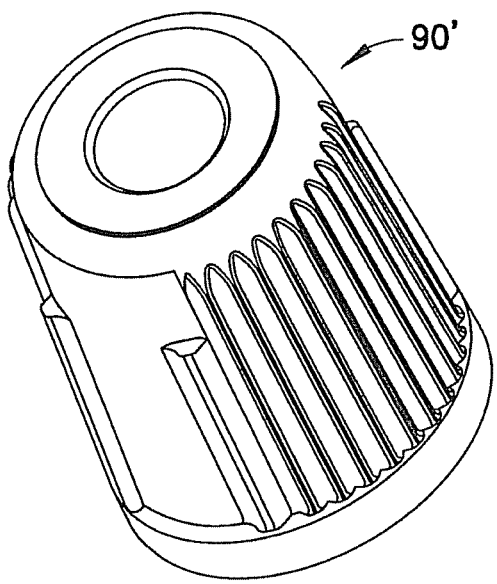
FIG. 26 is an elevated perspective view of the cap assembly shown in FIGS. 18 and 19 according to a first alternative to the third embodiment of the present invention.
Figure 27:
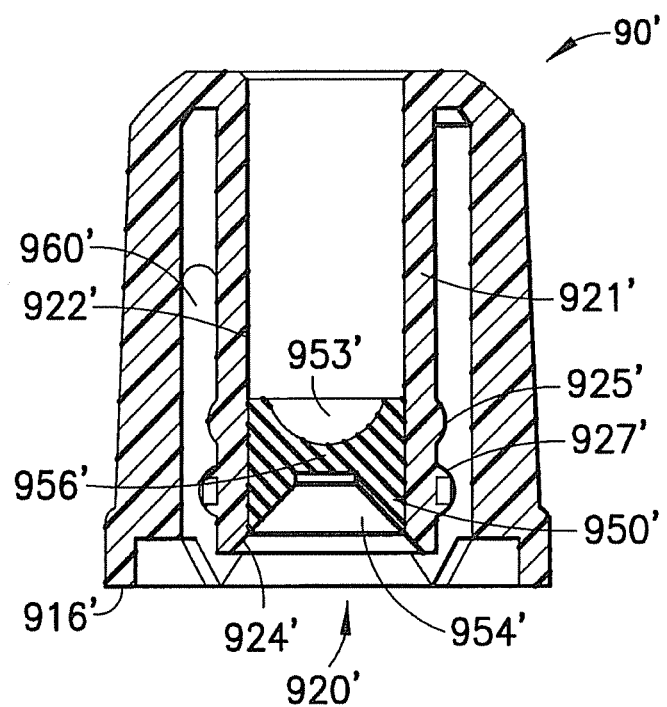
FIG. 27 is a vertical cross-sectional view of the cap assembly shown in FIG. 26.

Referring to FIGS. 26 and 27, an alternative cap assembly 90' according to the third embodiment is shown. As shown in FIG. 27, cap assembly 90' includes an internal annular ring portion 921' depending downward from a position proximate to the top of the cap assembly 90' such that channel 960' extends nearly an entire length of the cap assembly 90'. Bottom surface 916' does not include a recess for receiving the upraised surface 851 of the seating ledge of the collection tube 85. Stopper 950' is disposed entirely within the diameter of the interior surface 922' of the internal annular skirt portion 921' such that the stopper 950' is formed of a single portion having a cylindrical shape with a constant diameter. Stopper 950' includes an upper recess 953' and a lower, funnel-shaped recess 954' separated by a pierceable closure 956'. Stopper 950' is disposed within the cap assembly 90' such that the distance between the top surface of the cap assembly 90' and the funnel-shaped recess 954' corresponds to a distance between a contact surface 411 of a probe assembly 40 and aspiration hole 422 of a probe needle 420, as is shown in FIG. 22. Bottom surface 924' of internal annular skirt portion 921' is beveled upward so as to form a cooperating surface with the funnel-shaped recess 954'. An integrally molded annular elastomeric ring 927' surrounds the internal annular ring portion 921' between the bottom surface 924' and the protruding ring 925' and engages the second sidewall surface 885 of the internal cavity 880 of the collection tube 85 so as to seal the internal cavity 880 when the cap assembly 90' is disposed on the collection tube 85. Because the annular elastomeric ring 927' extends outward from the internal annular skirt portion 921' of the cap assembly 90', it positively engages the internal cavity 880 so as to form a better seal with the internal cavity 880.

Figure 28:
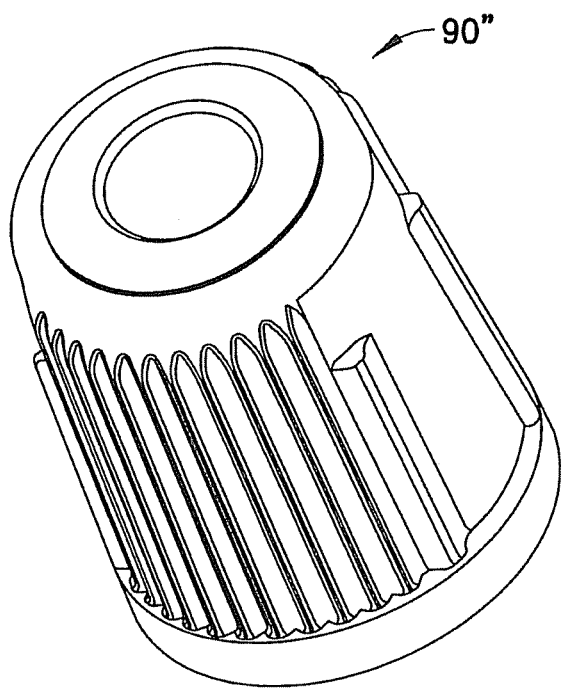
FIG. 28 is an elevated perspective view of the cap assembly shown in FIGS. 18 and 19 according to a second alternative to the third embodiment of the present invention.
Figure 29:
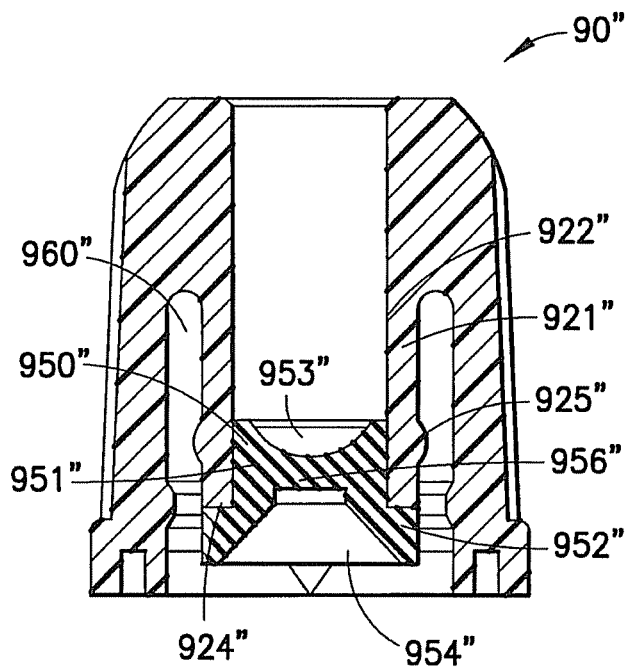
FIG. 29 is a vertical cross-sectional view of the cap assembly shown in FIG. 28.

Referring to FIGS. 28 and 29, another alternative cap assembly 90" according to the third embodiment is shown. As shown in FIG. 29, cap assembly 90" includes an internal annular ring portion 922" that is relatively long in comparison to the internal annular ring portion 922 of the cap assembly 90, discussed above. Stopper 950" is integrally molded with the internal annular skirt portion 921" of the cap assembly 90" at the interior surface 922" and bottom surface 924". The upper portion 951" of the stopper 950" includes a recess 953" defined therein and is relatively large in comparison to the lower portion 952" of the stopper 950". As such, the lower, funnel-shaped recess 954" is formed within both the lower and upper portions 952", 951" of the stopper 950". Upper recess 953" and lower, funnel-shaped recess 954" are separated by a pierceable closure 956". Because the internal annular skirt portion 921" is relatively long, the protruding ring 925" is not formed immediately adjacent to the bottom surface 924" of the internal annular skirt portion 921". Stopper 950" is disposed within the cap assembly 90" such that the distance between the top surface of the cap assembly 90" and the funnel-shaped recess 954" corresponds to a distance between a contact surface 411 of a probe assembly 40 and aspiration hole 422 of a probe needle 420, as is shown in FIG. 22. When the cap assembly 90" is disposed on the collection tube and the upper portion 860 of the collection tube 85 is engaged within the channel 960", the internal annular skirt portion 921" and stopper 950" extend into the internal cavity 880 such that the stopper 950" seals the internal cavity, as described above with respect to cap assembly 90 and shown in FIG. 20. Cap assembly 90" may also include one or more protruding annular rings disposed on the interior sidewall of the external annular skirt portion for frictionally engaging the upper portion 860 of the collection tube 85 so as to secure the cap assembly 90" on the collection tube 85.

It is to be appreciated, that the cap assemblies 90, 90', 90" according to the third embodiment described above can be used with a variety of collection containers or microtubes other than the collection tube 85. Stoppers 950, 950', 950" of cap assemblies 90, 90', 90" are provided with funnel-shaped or conical recesses 954, 954', 954" disposed within the cap assemblies 90, 90', 90" at a fixed distance corresponding to the distance between the contact surface 411 and aspiration hole 422 of a standard probe assembly 40 so as to funnel the blood or specimen sample toward the probe assembly 40 during transfer of the blood or specimen sample to a testing instrument. Thus the cap assemblies 90, 90', 90" according to the third embodiment of the present invention eliminate the known dead volume of conventional microtube or collection container caps such that less blood or specimen sample is required to be collected and more tests can be performed on a lower volume of the blood or specimen sample.

Figure 43:
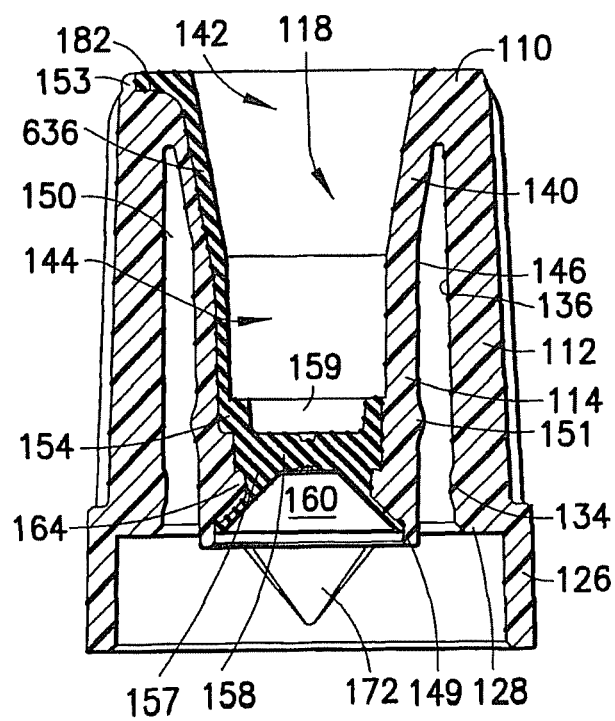
FIG. 43 is a cross-sectional side elevation view of a second shot of molded material for the cap assembly shown in FIG. 30.
Figure 44:
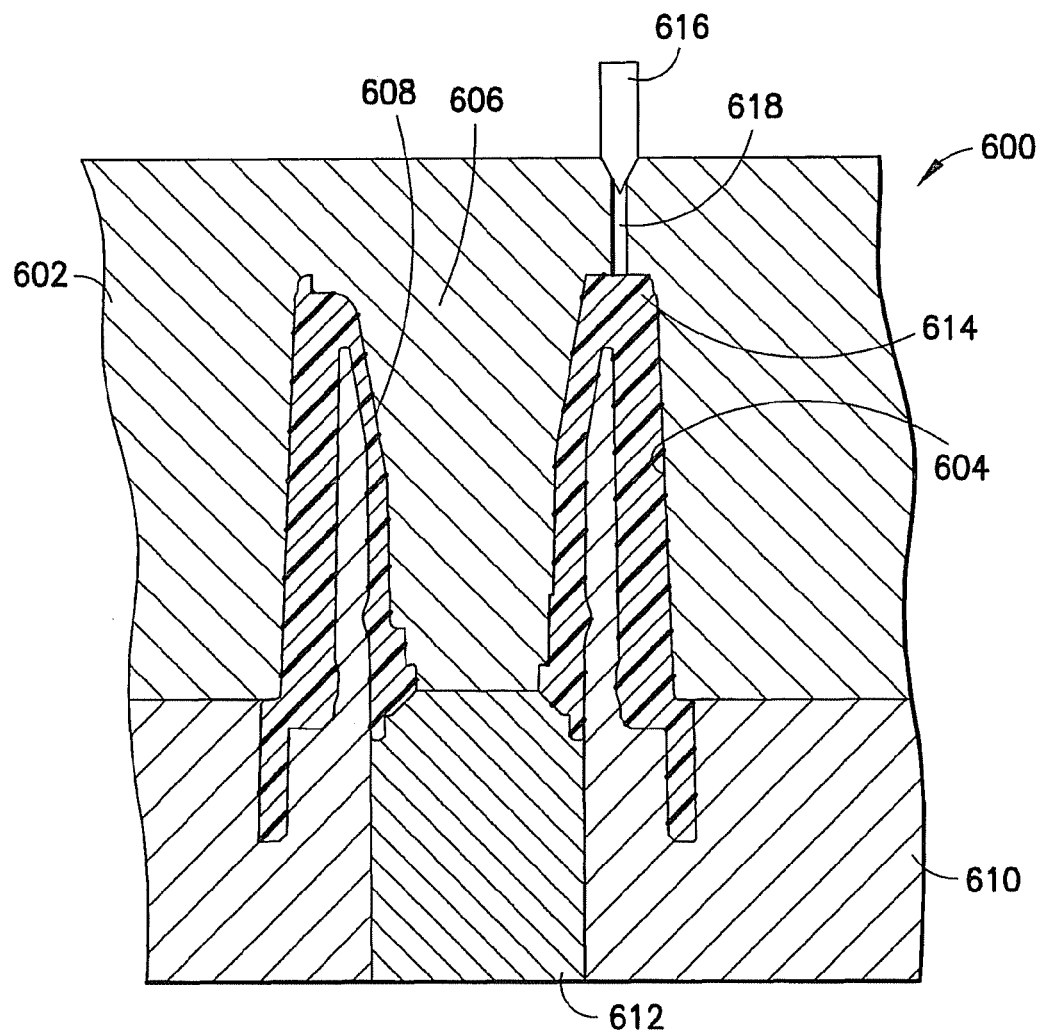
FIG. 44 is a cross-sectional elevation view of the molding assembly for molding the first shot of molding material shown in FIGS. 38 and 42.
Figure 45:
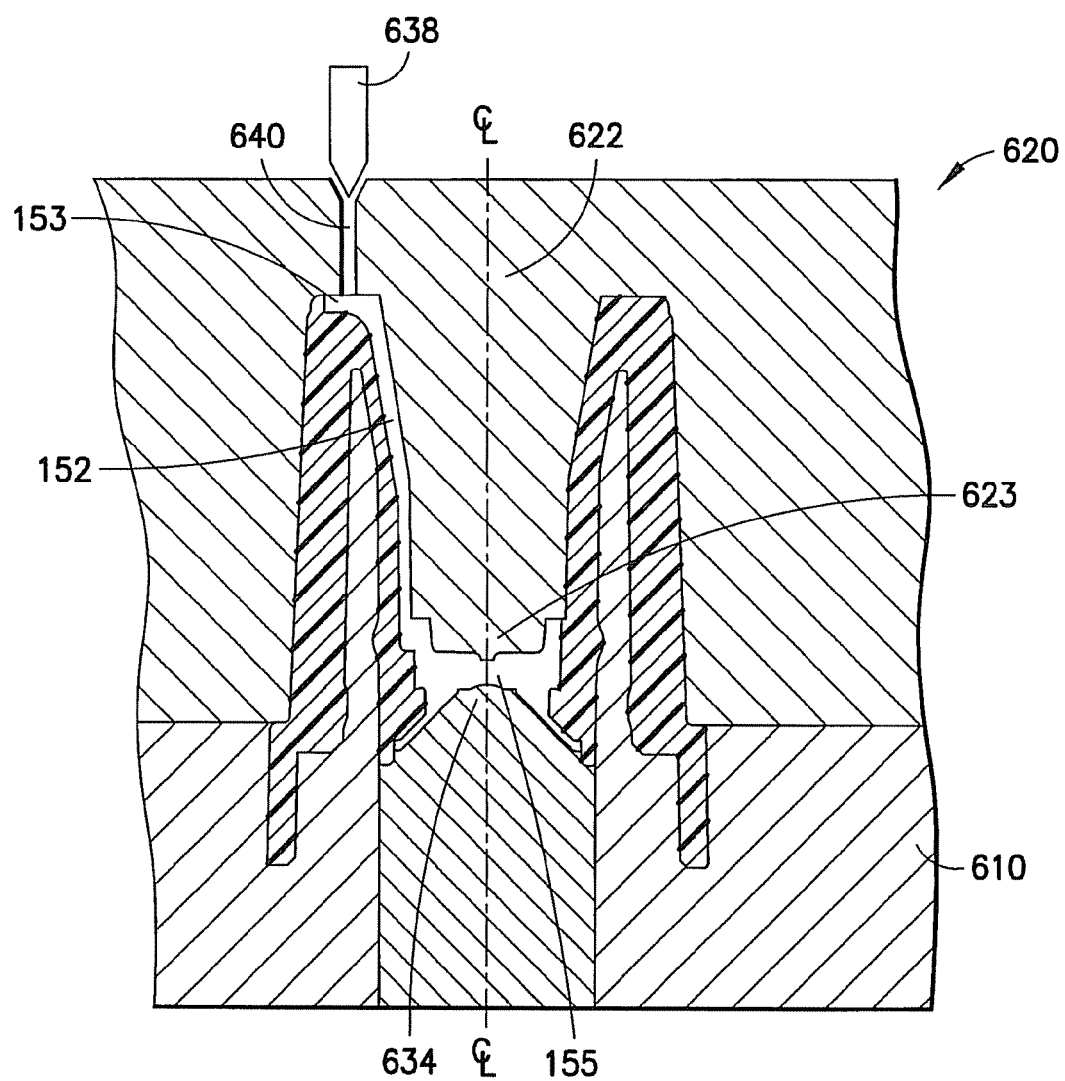
FIG. 45 is a cross-sectional elevation view of the molding assembly during molding of the second shot of molding material shown in FIGS. 39 and 43.

With reference to FIGS. 30-43 and 48 there is shown a collection device 1000 having a cap assembly 100 according to a fourth embodiment of the invention. The collection device 1000 includes a collection tube 104, which is preferably tubular in shape, comprising a closed bottom 105, an open top portion 102, and a sidewall 107 extending circumferentially between the open top portion 102 and the closed bottom 105. The collection tube 104 is configured for receiving a specimen sample therein, such as blood. According to one embodiment, the collection tube 104 may include at least one capillary channel as discussed in detail above in relation to FIGS. 3, 5-6, 11, and 20. FIGS. 44 and 45 show a method of co-molding the cap assembly of FIGS. 30-43 and 48. The method of co-molding the cap assembly 100 according to the present invention is particularly advantageous as it allows for consistent molding of the pierceable portion, i.e., septum, within the cap assembly.

Figure 30:
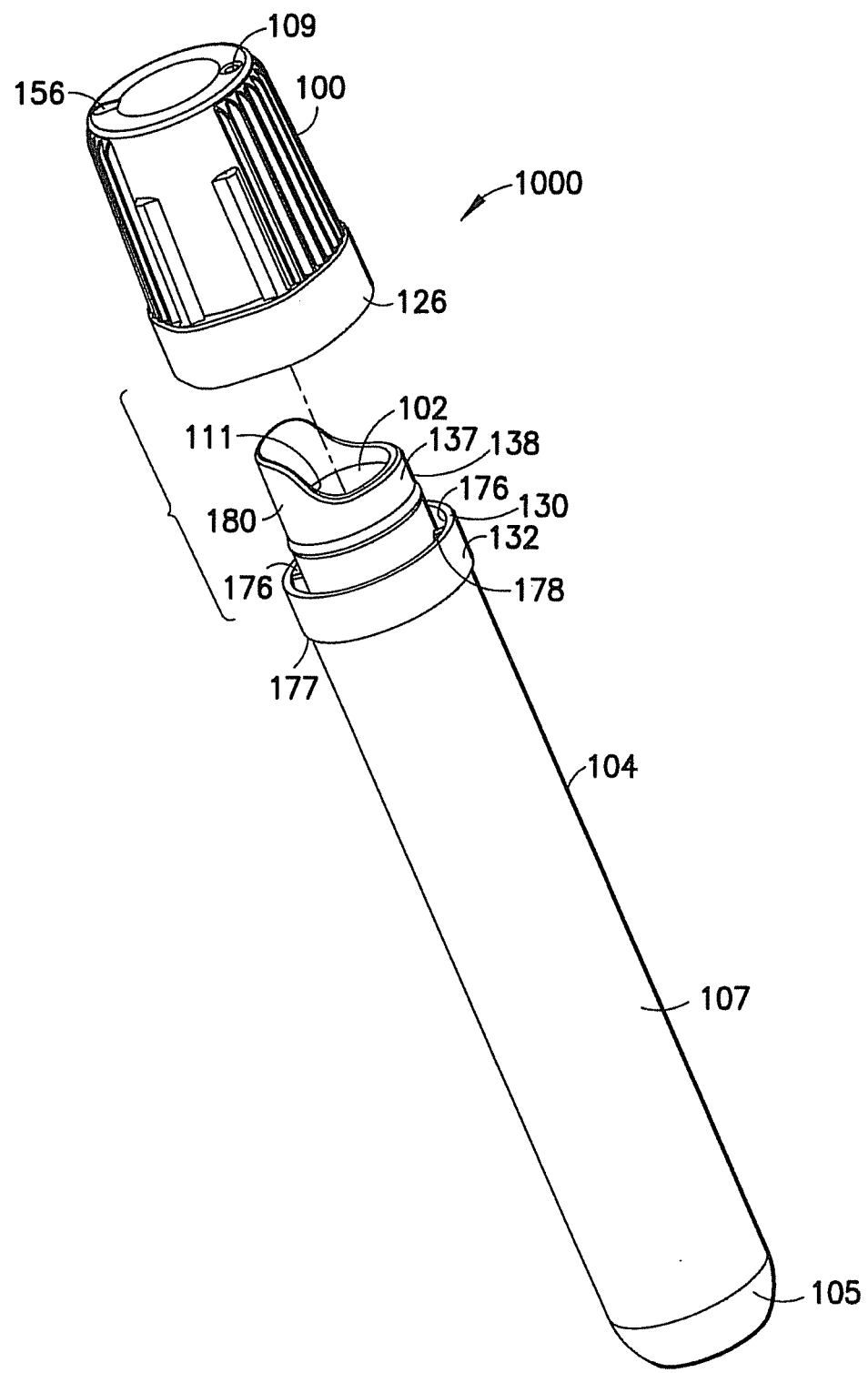
FIG. 30 is an exploded perspective view of the collection device pursuant to a fourth embodiment of the invention.
Figure 31:
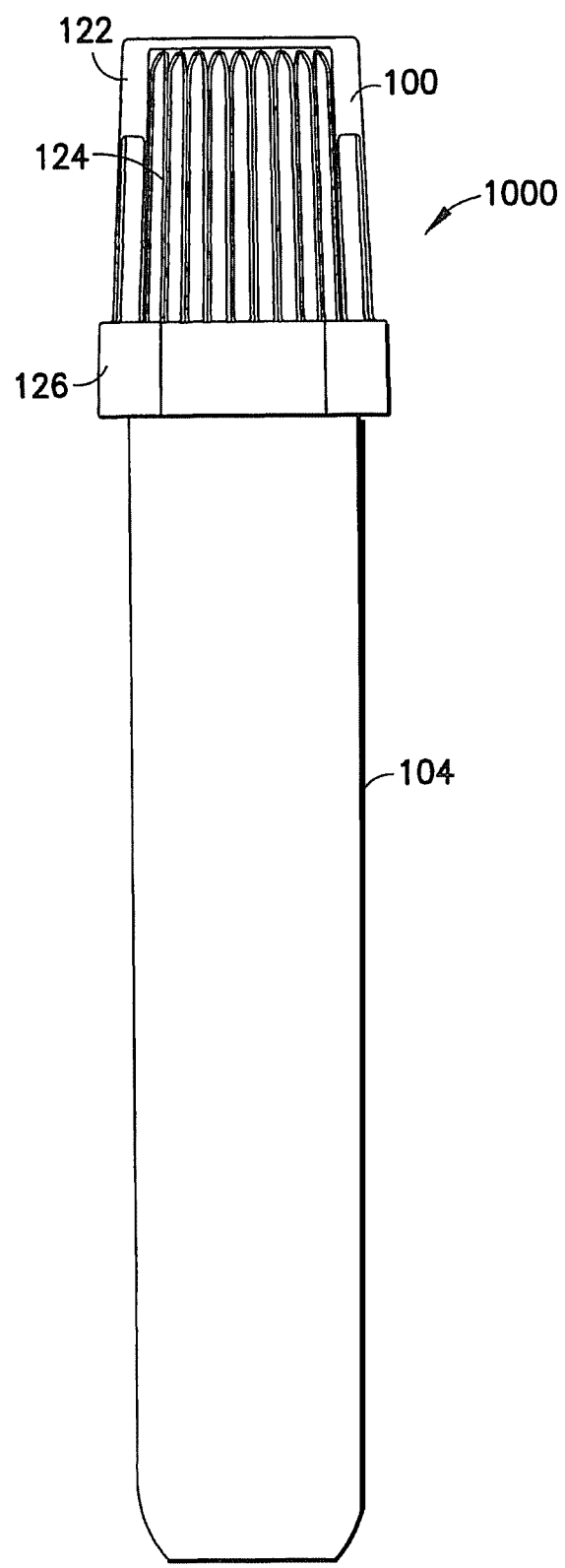
FIG. 31 is a front elevation view of the collection device shown in FIG. 30.
Figure 32:
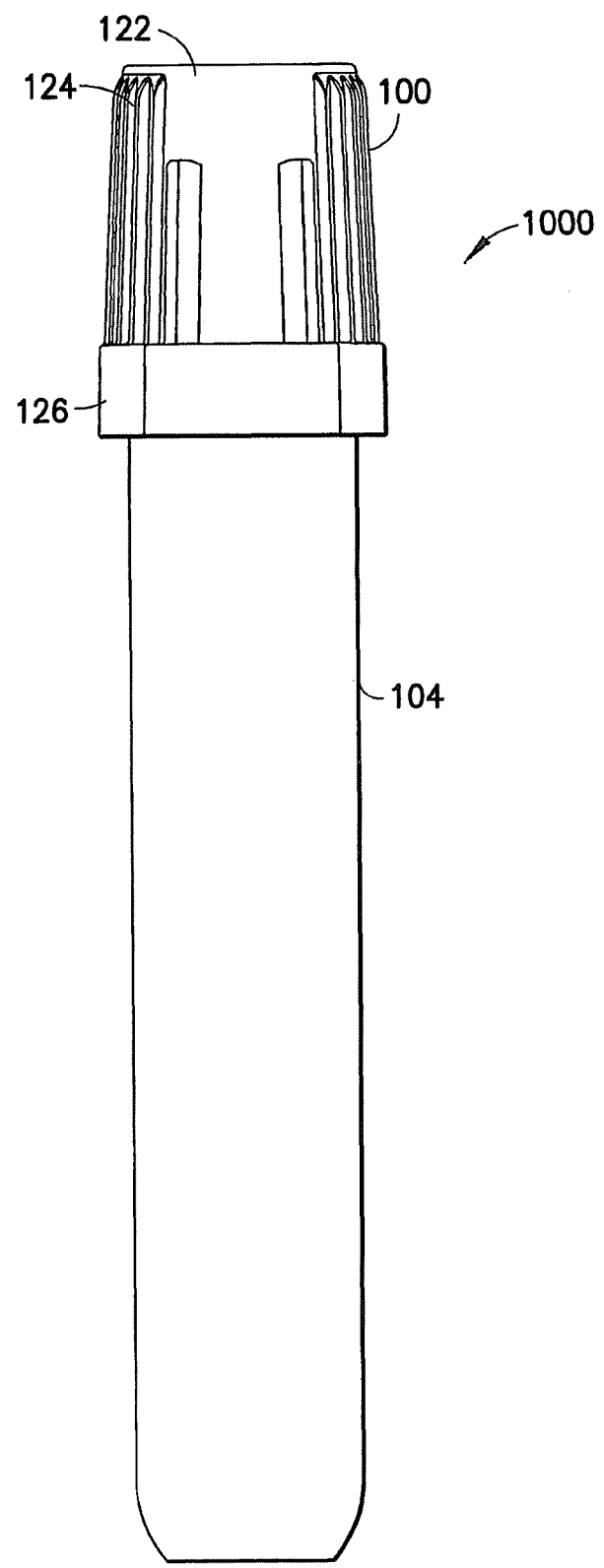
FIG. 32 is a side elevation view of the collection device shown in FIG. 30.
Figure 33:
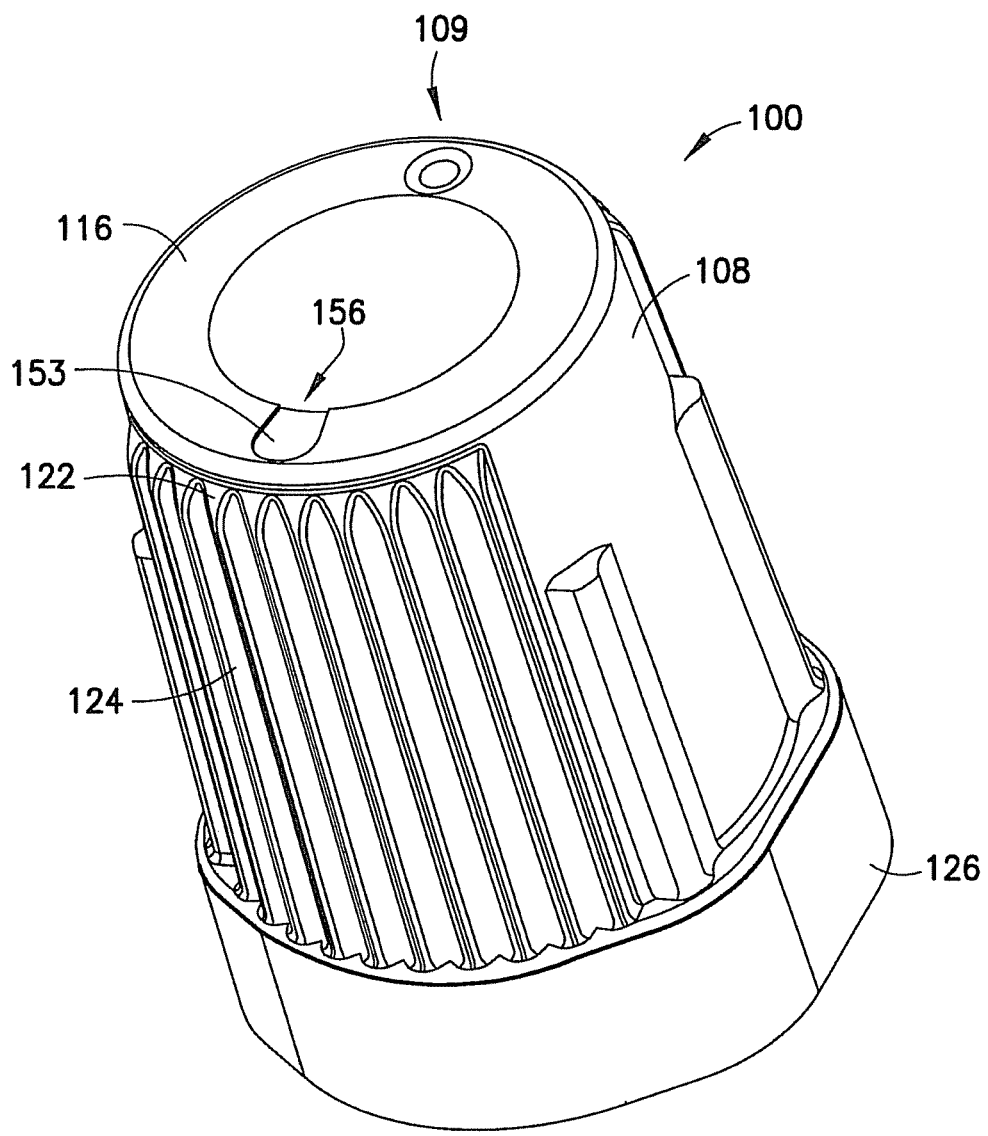
FIG. 33 is an elevated perspective view of the cap assembly shown in FIG. 30.
Figure 34:
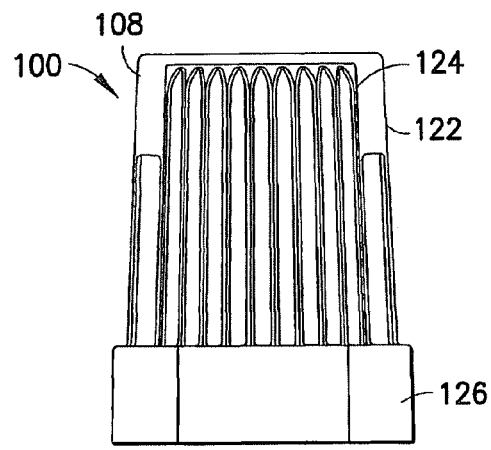
FIG. 34 is a front elevation view of the cap assembly shown in FIG. 30.
Figure 35:
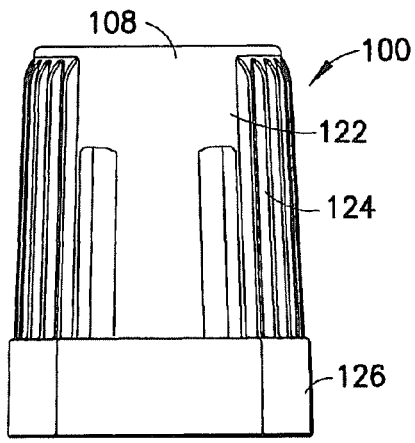
FIG. 35 is a side elevation view of the cap assembly shown in FIG. 30.
Figure 36:
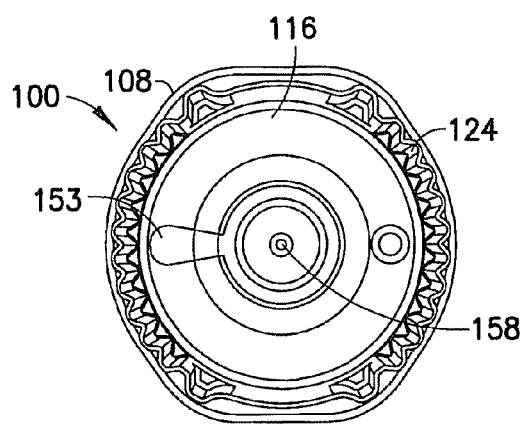
FIG. 36 is a top view of the cap assembly shown in FIG. 30.
Figure 48:
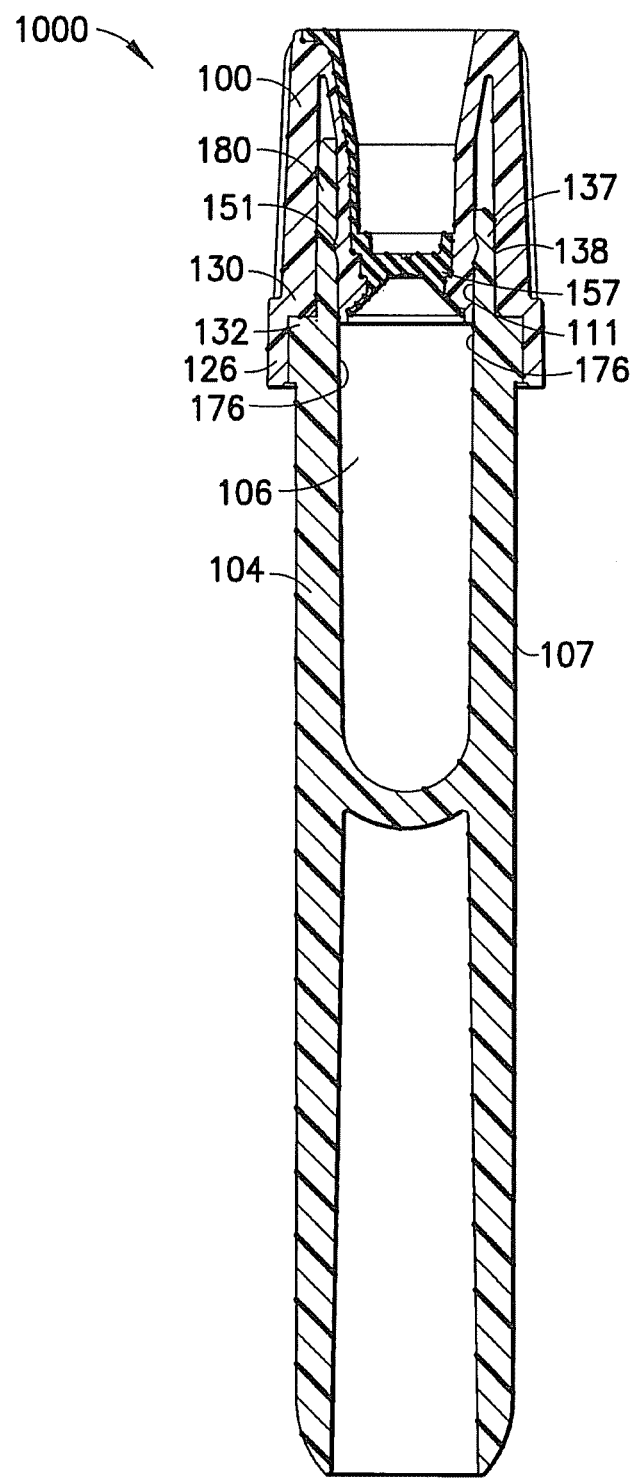
FIG. 48 is a cross-sectional elevation view of the cap assembly and tubular member of FIG. 31.

With reference to FIGS. 30 and 48, a collection device 1000 having a cap assembly 100, as particularly shown in FIGS. 31-39 and 42-43, is provided for covering the top opening 102 of the collection tube or container 104 and sealing the internal cavity 106 of collection tube 104, as shown in FIG. 48. As shown in FIGS. 33-36 and 38-43, cap assembly 100 is formed from a first molding material and includes an outer cap 108 having a ring-shaped top covering portion 110 and an external annular skirt portion 112 depending from the top covering portion 110. According to one embodiment, the first molding material is preferably injected from a first injection site 109 as shown in FIGS. 33 and 44. The top covering portion 110 defines a top surface 116 of the outer cap 108 and includes an interior cavity 118 extending through the top covering portion 110 from the top surface 116 to a bottom opening 120 in the outer cap 108. External annular skirt portion 112 and top covering portion 110 define an exterior surface 122 of the cap assembly 100. Preferably, gripping features 124 such as raised ridges or knurling are provided on the exterior surface 122 to assist in placement and removal of the cap assembly 100 on the collection tube 104. External annular skirt portion 112 has a bottom surface or collar 126 which is stepped outward to create a bottom stop ledge 128 for contacting a top surface 130 of a collar 132 on the collection tube 104, as shown in FIGS. 30 and 48, wherein the collar 132 of the collection tube 104 is essentially concentric with and contained within the collar 126 of the cap assembly 100. A plurality of protrusions 134 are provided on the interior surface 136 of the external annular skirt portion 112 for frictionally engaging the exterior sidewall surface 138 of the collection tube 104 when the outer cap 108 is disposed over the collection tube 104 so as to retain the cap assembly 100 in place on the collection tube 104.

Outer cap 108 also includes an internal annular skirt portion 114 depending from the top covering portion 110 and into the cavity 118. The internal annular skirt portion 114 includes a ramped portion 140 at a top portion thereof to form an opening 142 having a larger diameter at the top covering portion 110 or opening 102 which funnels down to create an opening having a narrower diameter opening or portion 144 toward the bottom of the cavity 118. At this narrower portion 144, the internal annular skirt portion 114 is partially co-extensive with the external annular skirt portion 112. Internal annular skirt portion 114 has an outer surface 146 spaced from the interior surface 136 of the external annular skirt portion 112 so as to form a channel 150 between the external and internal annular skirt portions 112, 114. An annular protruding ring 151 may also be provided on the exterior surface 146 of the internal annular skirt portion 114 at the base thereof for frictionally engaging the internal sidewall surface 111 of the internal cavity 106 of the collection tube 104 when the cap assembly 100 is disposed on the collection tube 104 so as to retain the cap assembly 100 in place.

Figure 41:
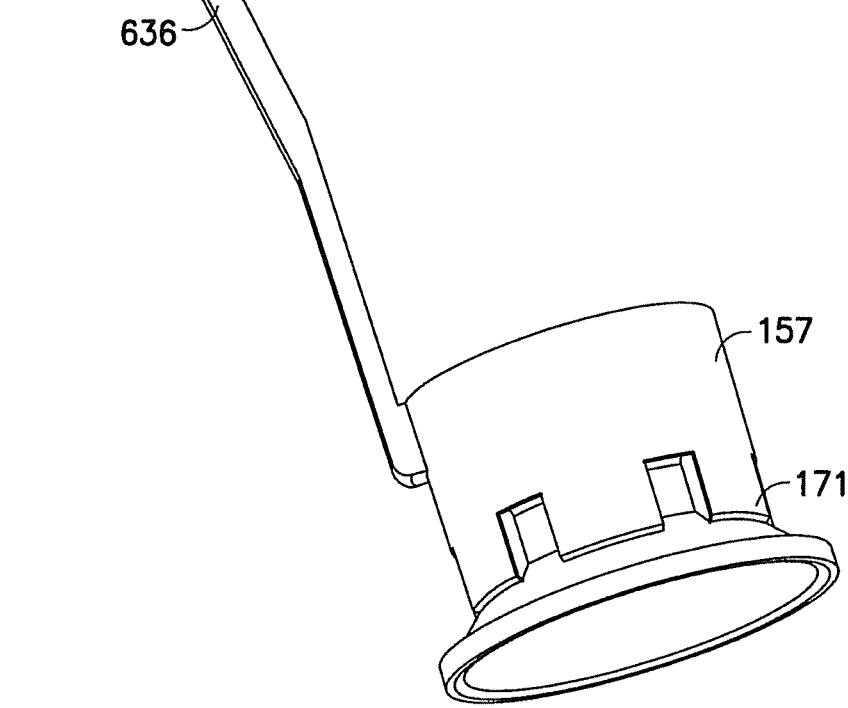
FIG. 41 is a side perspective view of the second shot of molded material shown in FIG. 39.
Figure 42:
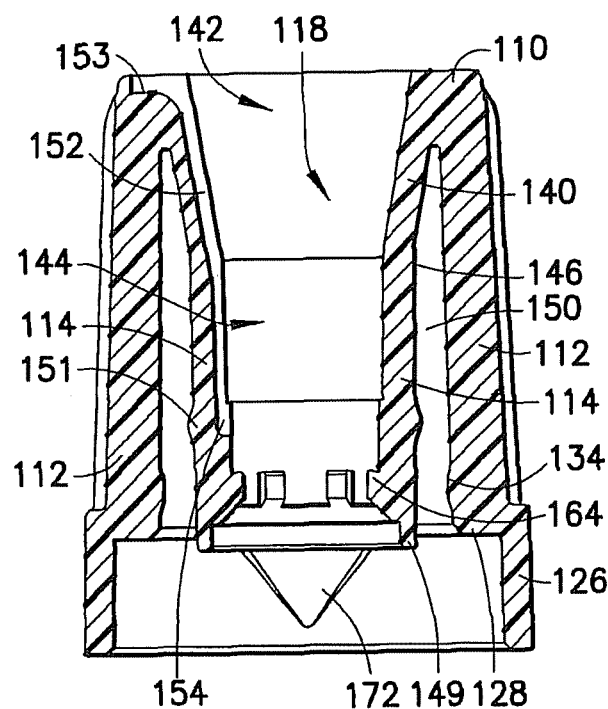
FIG. 42 is a cross-sectional side elevation view of a first shot of molded material for the cap assembly shown in FIG. 30.

With continuing reference to FIGS. 33, 38, 42, and 44, a flow channel 152 is defined within a portion of the cap body or outer cap 108. In particular, the flow channel 152 can extend through a portion of the internal annular skirt 114. The flow channel 152 includes an inlet 153 and an outlet 154. The outlet 154 is positioned adjacent to a target location 155 within the internal cavity 118 of the outer cap 108. According to one embodiment, the flow channel 152 is molded as an indentation within the interior wall surface 148 of the internal skirt 114 and extends along this interior wall surface 148 approximately the entire height of the outer cap 108. The flow channel inlet 153 can extend through the top covering portion 110 of the outer cap 108 to provide a second injection site 156, as illustrated in FIGS. 33, 43, and 45, for injection of the second molding material. This second molding material is injected from the flow channel inlet 153 into the flow channel 152 and flows out of the flow channel outlet 154 to the target location 155 to form a stopper 157 having a pierceable portion or septum 158, as described in detail below. A portion of the second molding material, as shown by 159 in FIGS. 39 and 41, can remain within the flow channel 152 after molding so as to form a substantially continuous inner surface 148 of internal skirt 114.

As shown in FIGS. 39, 41, and 48, the stopper 157 is integrally formed with the interior wall surface 148 of the internal annular skirt portion 114. Stopper 157 is disposed entirely within the diameter of the interior surface 148 of the internal annular skirt portion 114 such that the stopper 157 is formed of a single portion having a cylindrical shape with a substantially constant diameter. Stopper 157 includes an upper recess 159 and a lower, funnel-shaped conical recess 160 separated by the pierceable closure or septum 158. The conical recess 160 is in communication with a collection cavity 106 within the collection tube 104.

Figure 46:
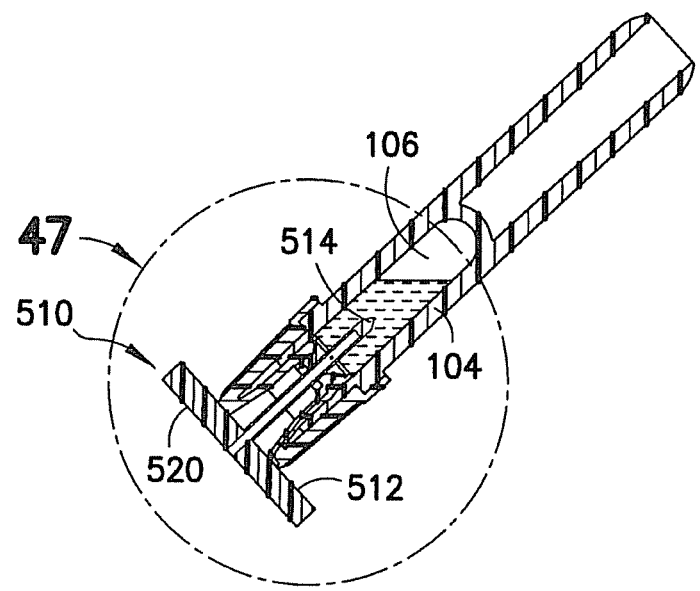
FIG. 46 is a partial cross-sectional view of the device for capillary collection of blood samples shown in FIG. 31 with the device oriented for transferring a sample to a testing device and a probe assembly inserted into the device.
Figure 47:
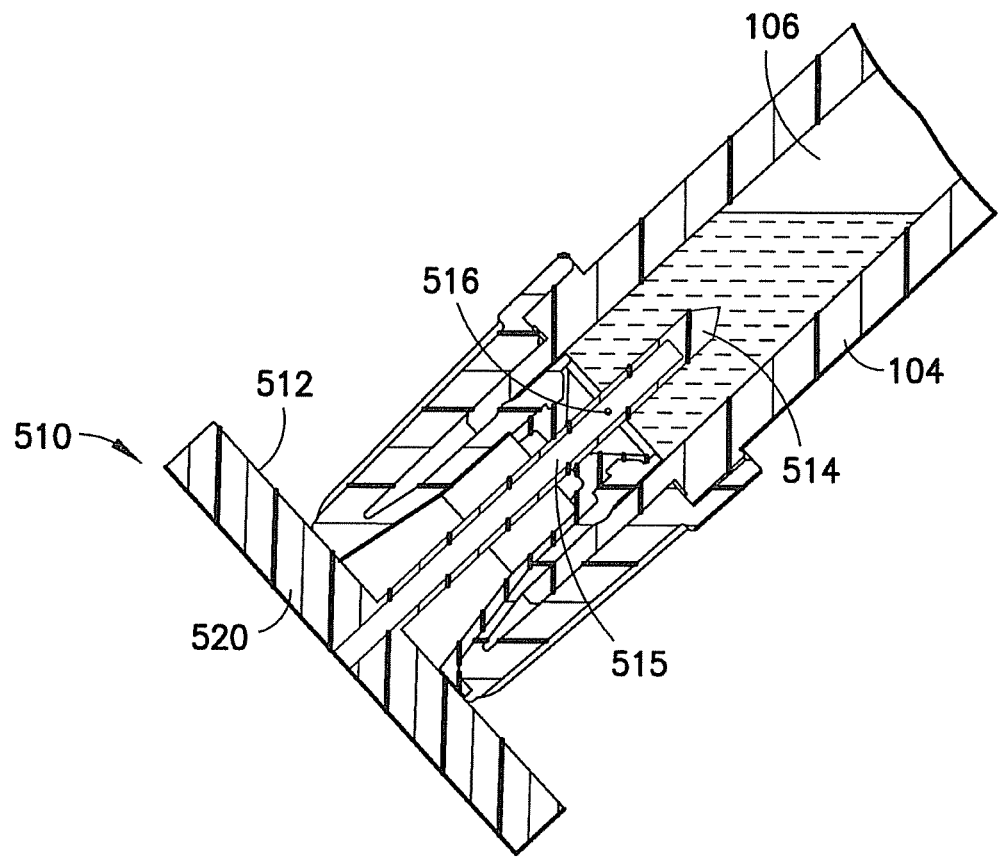
FIG. 47 is a detailed partial cross-sectional view of area "47", shown in FIG. 46.

Stopper 157 is disposed within the cap assembly 100 such that the distance between the top surface 116 of the cap assembly 100 and the funnel-shaped recess 160 corresponds to a distance between a contact surface 512 of a probe assembly 510 and aspiration hole 516 of a probe needle 514, as is shown in FIGS. 46 and 47. Bottom surface 149 of internal annular skirt portion 114 is beveled upward so as to form a cooperating surface with the funnel-shaped recess 160. The funnel-shaped conical recess 160 enables the retrieval of substantially all of the biological sample container within the collection tube 104.

Referring to FIGS. 38-41, the bottom surface 149 of the internal annular skirt 114 includes at least one protrusion 164 extending inwardly into the cavity 118 adjacent the target location 155 to integrally join the second molding material forming the stopper 157 to the first molding material forming the outer cap 108 to provide a mechanical interlock and improve the chemical adhesion of the outer cap 108 with the stopper 157. In addition to this at least one protrusion 164 at the bottom surface 149 of the internal annular skirt 114, a corresponding indentation 168 is provided on either side of the protrusion 164 which allows for the flow of the second molding material to enter into these indentations 168, as shown by 171 in FIGS. 39 and 41.

Figure 37:
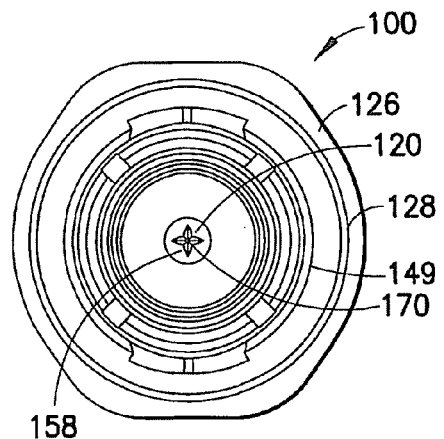
FIG. 37 is a bottom view of the cap assembly shown in FIG. 30.

The formation of the stopper 157 by flowing the second molding material through the flow channel 152 results in reproducible results and better control of the molding such that the pierceable septum 158 can have the shape of a star 170, as best shown in FIG. 37. This particular star shape 170 facilitates tearing/piercing of the septum. It is contemplated herein that a plurality of various star configurations would assist in the tearing/piercing of the septum by increasing the boundary and distributing the forces of an applied puncture tip thereon.

Preferably, outer cap 108 is formed from a hard plastic or composite material, such as a high density polyethylene, while stopper 157 is formed from a soft plastic or thermoplastic elastomer material so as to render the septum 158 of the stopper 157 pierceable and eliminate air bubbles in the hematology instrument. Furthermore, this thermoplastic elastomer material of the stopper 157 produces a septum 158 that is easily pierceable by a standard probe needle 514 (shown in FIGS. 46 and 47) and has the ability to re-seal after the probe needle 514 is removed from the stopper 157. Additionally, the thermoplastic elastomer material is such that vestige from the probe needle 514 is removed as it is withdrawn through the septum 158, thus reducing the risk of undesirable exposure to the biological sample.

As shown in FIGS. 30, 40, and 42-43, at least one triangular-shaped cam member 172 extends downwardly from a bottom portion 174 of the external annular skirt portion 112. As particularly shown in FIG. 30, the collar 132 of tube 104 includes an interior portion 176 and a base surface 177. At least one triangular-shaped cam member 178 extends in an upward position from the base surface 177 and adjacent the interior portion 176 with the collar 132. Triangular-shaped cam members 172 and 178 are configured to cam against each other to lock the cap assembly 100 onto the collection tube 104. The cap assembly 100 may be unseated from the base 177 of the collar 132 on the tube 104 by twisting the cap assembly 100. According to one embodiment, these triangular-shaped members 172, 178 have an extended length such that only two sets of the triangular-shaped members 172, 178 are needed, wherein the sets are positioned at 180° with respect to each other, to adequately secure the cap assembly 100 onto the collection tube 104.

As shown in FIGS. 30 and 48, the top portion of the collection tube 104 or tubular sidewall includes a collection funnel 180. Collection funnel 180 acts as a scoop, which can be positioned adjacent to a puncture point in a person's body for facilitating the flow of a biological sample, such as blood, from the puncture point into the collection tube 104. As discussed above, the cap assembly 100 includes a channel 150 created between the external and internal annular skirt portions 112, 114. The cap assembly 100 is positioned on the collection tube 104 such that the channel 150 receives the upper portion 137 of the collection tube 104 and the top surface 130 of collar 132 contacts stop ledge 128 of the external annular skirt portion 112. This channel 150 has a predetermined height and/or is configured to receive the collection funnel 180 therein.

The cap assembly 100 is positioned on the collection tube 104 such that the collection funnel 180 as well as the upper portion 137 of the collection tube 104 are engaged by the internal and external annular skirt portions 112, 114 of the outer cap 108 such that the internal annular skirt portion 114 extends into the top opening 102 of the collection tube 104 and engages the internal surface 111 of the collection tube 104. The lower portion of stopper 157 depends further into the internal cavity 106 so as to engage and seal the internal cavity 106.

It is to be appreciated that the collection device 1000 described above can be used in a similar manner as described above with respect to the devices 10, 60, and 80 according to the first, second, and third embodiments, respectively, with the blood or specimen sample being collected via the collection funnel or curved receiving portion 180 of the upper or lip portion 137 of the collection tube 100. Referring to FIGS. 46 and 47, the blood or specimen sample contained within the internal cavity 106 of the collection tube 100 is transferred to the testing instrument, such as a hematology instrument, via a probe assembly 510. As noted above, the collection device 1000 is compatible with standard testing instruments such that the device can be connected to the testing instrument via automated assembly features of the testing instrument. As shown in FIGS. 46 and 47, during automated or manual assembly, the device 1000 is inverted at a 45° angle. A probe needle 514 having an internal cannula 515 and an aspiration hole 516 is then inserted into the internal cavity 106 of the collection tube 104.

As shown in FIGS. 46 and 47, when inserted, the probe needle 514 extends through the interior cavity 118 in the outer cap 108 of the cap assembly 100 and the recess 159 in the upper portion of the stopper 157 such that it pierces the pierceable closure or septum 158 in the stopper 157. Collection device 1000 is positioned on probe assembly 510 such that a contact surface 512 of the base portion 520 of probe assembly 510 engages the top surface 116 of the outer cap 108. According to the present embodiment, stopper 157 is disposed on the internal annular skirt portion 114 of the outer cap 108 within the interior cavity 118 such that a fixed length L measured from the top surface 116 of the outer cap 108 to the funnel-shaped recess 160 in the lower portion of the stopper 157 corresponds to the distance between the contact surface 512 of the probe assembly 510 and the aspiration hole 516 along the probe needle 514. In this manner, the aspiration hole 516 of the probe needle 514 is positioned within the funnel-shaped recess 160 of the stopper 157 such that the aspiration hole 516 is in communication with the funnel-shaped recess 160 and internal cavity 106.

Due to the inverted position of the collection tube 104 and stopper 157, the blood or specimen sample contained within the internal cavity 106 will flow downward toward the aspiration hole 516. Internal ribs, as shown in FIGS. 3, 5-6, and 11 may be disposed on the internal sidewall surface of the collection tube 104 to assist in the downward flow of the sample by promoting capillary flow along the internal sidewall surface and channeling the blood or specimen sample onto the funnel-shaped recess 160 of the stopper 157. It is noted that the present invention is not limited to collection tubes, which have internal ribs and may be used with other types of tubes in conjunction with the cap assembly 100 of the present invention.

Preferably, the funnel-shaped recess 160 of the stopper 157 is formed at a 45° angle to promote funneling of the blood or specimen sample from within the collection tube 104 toward the aspiration hole 516 of the probe needle 514. Also, the angle of the funnel-shaped recess 160 helps to push up dead volume in the flow of the blood or specimen sample toward the aspiration hole 516. Thus, funnel-shaped recess 160 of stopper 157 acts as a space elimination feature within the stopper 157, which positions the blood or specimen sample at the aspiration hole 516 of the probe needle 514. The space elimination feature of the funnel-shaped recess 160 thus operates to maximize the low volume of the blood or specimen sample contained within the internal cavity 106 of the collection tube 104 and avoids waste or non-utilization of collected blood or specimen samples.

As stated above, it is to be appreciated that the cap assembly 100 according to the fourth embodiment described above can be used with a variety of collection containers or microtubes. The stopper 157 of cap assembly 100 is provided with a funnel-shaped or conical recess 160 disposed within the cap assembly 100 at a fixed distance corresponding to the distance between the contact surface 512 and aspiration hole 516 of a standard probe assembly 510 so as to funnel blood or specimen sample toward the probe assembly 510 during transfer of the blood or specimen sample to a testing instrument. Thus the cap assembly 100 according to the fourth embodiment of the present invention eliminates the known dead volume of conventional microtube or collection container caps such that less blood or specimen sample is required to be collected and more tests can be performed on a lower volume of the blood or specimen sample.

Reference is now made to FIGS. 44 and 45 that illustrate cross-sectional views of a first and second molding arrangement for forming the two-shot molded cap assembly 100 of the invention. The method of forming the cap assembly comprises providing a first mold arrangement, generally illustrated as 600 in FIG. 44, comprising a top mold member 602 having a first shape defining a first cavity 604 for molding an outer cap 108. The mold 600 includes a bottom mold member 610 having a core pin 612, which is movable with respect to the bottom mold member 610. The first and second mold members 602, 610 form a cavity for molding the outer cap 108 having a top covering portion 110, an internal annular skirt portion 114, and an external annular skirt portion 112. The top mold member includes an internal portion 606 for defining an interior cavity 118 of the outer cap 108, as shown in FIGS. 38 and 42. The top mold member 602 includes a channel forming portion 608 for forming a flow channel 152 in the interior surface 148 of the internal skirt 114. This flow channel 152 includes an inlet 153 and an outlet 154 and extends along this interior surface 148 substantially the entire vertical height of the internal skirt portion 114. The inlet 153 of the flow channel 152 can be located through the top covering portion 110 and the outlet 154 of the flow channel 152 is positioned adjacent to a target location 155 within the interior cavity 118 of the outer cap 108, as shown in FIGS. 38 and 42. The top mold member 602 includes a gate opening 618 for feeding the first molding material 614 from a first gate 616 into the first mold cavity 604.

The method further includes providing a second mold arrangement, generally illustrated as 620 as shown in FIG. 45. This second mold arrangement 620 includes a top mold member 622 having an internal mold portion 624, which has a different shape than the internal mold portion 606 of the top mold member 602 of the first molding arrangement 600. According to one embodiment, internal mold portion 624 includes an outwardly extending cup-shaped protrusion or arcuate protrusion 625 for defining a cup-shaped indentation in the stopper 157. The mold 620 includes a bottom mold portion 610, which is typically the same bottom mold portion 610 of the first mold arrangement 600, having a movable core pin 632 including a frusto-conical top portion 634. It can be appreciated that this protrusion 625 on the internal mold portion 624 can have any desired shape and the top portion 634 of the core pin 632 can have any desired shape depending upon the desired shape of the pierceable portion or septum 158 of the stopper 157. During molding of the second shot or molding of the stopper 157, the core pin 632 is dropped down from the top mold member 622 to form an open portion or target location 155 to receive the second molding material 636 from a second gate 638 through a gate opening 640 in the top mold member 622. As shown in FIG. 45, flow channel 152 in the interior surface 148 of internal skirt portion 114 has an inlet 153 that extends from the top covering portion 110 to an outlet 154 which is located adjacent to target location 155 such that the second molding material 636 flows through the channel 152 to the target location 155 to form the stopper 157. According to one embodiment, the second gate 638 can be positioned with respect to the top covering portion 110 of the cap assembly at approximately 180° with respect to the first gate 616 so that injection site 156 of the second molding material 636 is approximately 180° with respect to the injection site 109, as shown in FIGS. 30 and 33.

The method includes the step of injecting the first shot of molding material 614 from the first gate 616 through the gate opening 618 into the first molding cavity 604 to form the outer cap 108 having the top covering portion 110, an opening 102 extending through a center portion, and a cavity 118 in communication with the opening 102. The outer cap has a flow channel 152 extending from the top covering portion 110 of the outer cap 108 to a target location 155 within the cavity 118. The method further includes replacing the top mold member 602 of the first mold arrangement 600 with the top mold member 622 of the second mold arrangement 620 and replacing core pin 612 with core pin 632 and moving core pin 632 down with respect to the bottom mold member 610. The method then includes injecting the second shot of molding material 636 from the second gate 638 through gate opening 640 into the flow channel 152 from the inlet 153 through the top covering portion 110 of the outer cap 108 such that the second molding material 636 flows through the flow channel to the target location 155. This second molding material forms the stopper 157 including a pierceable septum 158 within the cap assembly 100. After application of the second molding material 636 into the flow channel 152, at least a portion of the second molding material 636 remains within the flow channel. According to one embodiment, the second molding material 636 can completely fill the flow channel 152 from the inlet 153 to the outlet 154 so that the top portion 182 of the second molding material 636 forms a flush or flat surface with the top covering portion 110 of the outer cap 108, as shown in FIG. 39. Alternatively, a top portion 182 of the second molding material 636 can be positioned below the plane of the top covering portion 110 of the outer cap 108.

It is to be appreciated that the two-shot molding method described above is not limited to the specifically disclosed shape/style embodiment shown in the figures but may be used to form a variety of shaped cap assemblies, with or without pierceable septums.

According to the embodiment shown in FIGS. 38-43, the molding method includes injecting the first molding material 614 into the first mold arrangement 600 to form an external annular skirt portion 112 and an internal annular skirt portion 114. Each of the external and internal annular skirt portions 112, 114 depend from the outer perimeter and an inner portion, respectively, of the top covering portion 110 and at least a portion of the internal annular skirt portion 114 defines the target location 155. The second molding material 636 is injected into the second mold arrangement 620 from the second gate 638 which is positioned at a location which is offset with respect to a longitudinal centerline CL, as shown in FIG. 45, extending through the target location 155.

Figure 40:
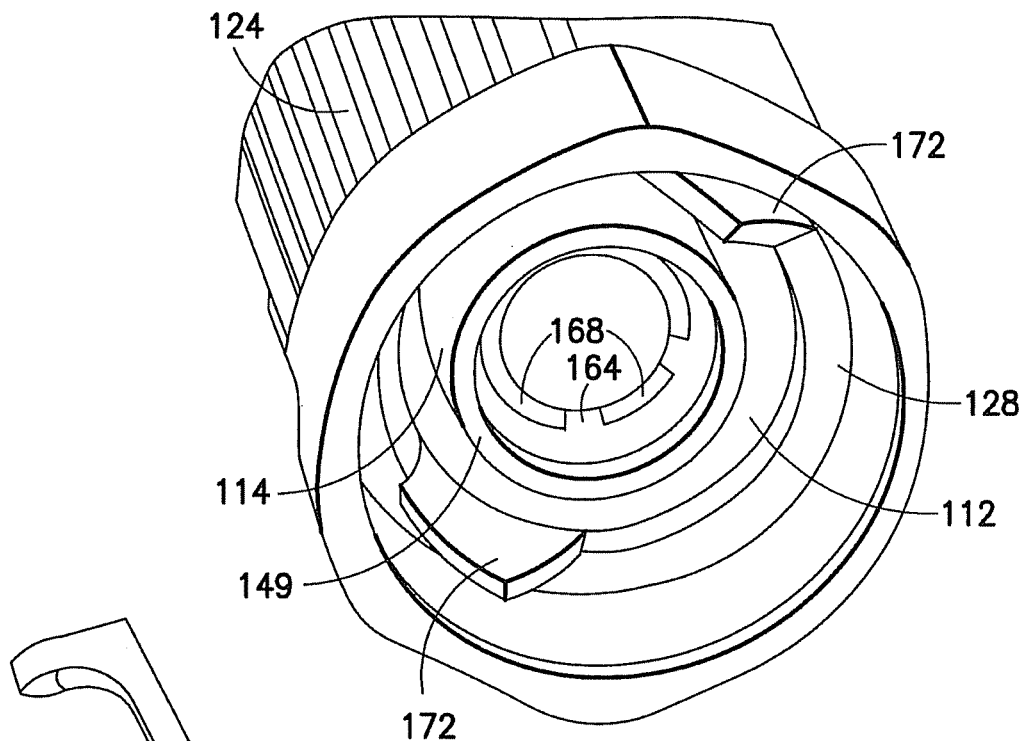
FIG. 40 is a bottom perspective view of the first shot of molded material shown in FIG. 38.

As shown in FIGS. 38 and 40, molding of the internal annular skirt portion 114 includes providing protrusions 164 adjacent the target location 155. As a result of this molding design, the second molding material 636 flows to the target location 155 into indentations 168 surrounding protrusions 164 so that the stopper 157, as shown in FIGS. 41 and 43, forms an interlocking mechanical/chemical bond with the protrusions 164 and consequently with the internal annular skirt portion 114 of the outer cap 108. The particular design of the frusto-conical portion 634 of the core pin 632 and the feeding of the second molding material 636 through flow channel 152 causes this second molding material 636 to flow to the target location 155 to form a star-shaped septum 158, 170. This star-shape facilitates piercing/tearing of the septum 158, 170. The top mold member 602 can be designed to mold the external annular skirt 112 of the outer cap 108 to include at least one triangular-shaped member 172 extending downwardly from a bottom portion 174 thereof. As discussed in detail above, this at least one triangular-shaped member 172 is adapted for cooperating with at least one upwardly extending triangular-shaped member 178 on an upper portion of the collection tube or container 104 for locking the cap assembly 100 on the collection tube 104.

As stated above, the first molding material 614, forming the outer cap 108 can be formed from a hard plastic or composite material, such as a high density polyethylene, while the second molding material 636 forming the stopper 157 can be formed from a soft plastic or thermoplastic elastomer material so as to render the septum 158 of the stopper 157 pierceable and eliminate air bubbles in the hematology instrument. Furthermore, this thermoplastic elastomer material of the stopper 157 produces a septum 158 that is easily pierceable by a standard probe needle 514 (shown in FIGS. 46 and 47) and has the ability to re-seal after the probe needle 514 is removed from the stopper 157. Additionally, the thermoplastic elastomer material is such that vestige from the probe needle 514 is removed as it is withdrawn through the septum 158, thus reducing the risk of undesirable exposure to the biological sample.

While several embodiments of a device for capillary collection of blood samples and method were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

What is claimed is:

1. A closure, comprising:
   a closure assembly for closing and sealing a container, the closure assembly comprising:
      a cap body defining a permanent cavity therethrough and having a top portion defining an opening, the cavity in fluid communication with the opening, and a portion of the cap body defining a flow channel having an inlet and an outlet; and
      a stopper disposed within the cavity adjacent the outlet of the flow channel, the stopper having a pierceable portion formed of a material, wherein the material is adapted to flow through the flow channel of the cap body to form the pierceable portion.

2. The closure of claim 1, wherein the cap body is formed from a first molding material and the stopper is formed from a pierceable second molding material, the second molding material being different than the first molding material.

3. The closure of claim 1, wherein the flow channel inlet extends toward the top portion.

4. The closure of claim 1, wherein the inlet of the flow channel is offset with respect to a longitudinal centerline extending through the cavity of the closure assembly.

5. The closure of claim 1, wherein the stopper has a bottom surface and a conical recess defined within the stopper forming the pierceable portion.

6. The closure of claim 5, wherein the conical recess is in communication with an interior of the container when the closure assembly closes the container.

7. The closure of claim 5, wherein the stopper is positioned within the cavity at a predetermined location such that a distance between the top portion and the conical recess corresponds to a distance between a probe contact surface and an aspiration hole of a probe assembly.

8. The closure of claim 5, wherein the bottom surface has a conical shape such that the pierceable portion has an area of reduced thickness as compared to the thickness of another portion of the stopper.

9. The closure of claim 1, wherein the pierceable portion includes a star shape to facilitate piercing thereof.

10. The closure of claim 1, wherein the cap body is formed from a high density polyethylene and the stopper is formed from a thermoplastic elastomer.

11. A closure, comprising:
    a closure assembly for closing and sealing a container, the closure assembly comprising:
       a cap body having a top portion defining an opening extending therethrough;
       an external annular skirt depending from an outer perimeter of the top portion;
       an internal annular skirt depending from an inner portion of the top portion adjacent the opening, the internal annular skirt defining a permanent cavity in fluid communication with the opening in the top portion, and a portion of the internal annular skirt defining a flow channel having an inlet adjacent the top portion and an outlet; and
       a stopper disposed within the cavity adjacent the outlet of the flow channel, the stopper having a pierceable portion formed of a material, wherein the material is adapted to flow through the flow channel of the cap body to form the pierceable portion.

12. The closure of claim 11, further comprising a plurality of gripping members disposed in connection with an outer surface of the external annular skirt.

13. The closure of claim 11, wherein the flow channel inlet extends through the top portion.

14. The closure of claim 11, wherein the flow channel extends within an interior surface of the internal annular skirt.

15. The closure of claim 11, wherein the stopper is co-formed with a portion of an interior surface of the internal annular skirt.

16. The closure of claim 11, wherein the internal annular skirt includes a ramped portion defining a funnel-shaped cavity having a larger diameter adjacent the top portion and a smaller diameter adjacent the stopper.

17. A container assembly comprising:
    a collection container having a closed bottom, an open top portion, and a sidewall extending therebetween, adapted to receive a specimen sample therein; and
    a closure assembly for closing and sealing the open top portion of the collection container, the closure assembly comprising:
       a cap body defining a permanent cavity therethrough and having a top portion defining an opening, the cavity in fluid communication with the opening, and a portion of the cap body defining a flow channel having an inlet and an outlet; and a stopper disposed within the cavity adjacent the outlet of the flow channel, the stopper having a pierceable portion formed of a material, wherein the material is adapted to flow through the flow channel of the cap body to form the pierceable portion.

18. The container assembly of claim 17, wherein the inlet of the flow channel is offset with respect to a longitudinal centerline extending through the cavity of the cap assembly.

19. The container assembly of claim 17, wherein a top portion of the sidewall of the collection container comprises a collection lip funnel for facilitating flow of a sample into an interior of the collection container.

20. The container assembly of claim 19, wherein the cap body comprises an external annular skirt and an internal annular skirt extending from the top portion, defining a channel therebetween configured for receiving the top portion of the sidewall and the collection lip funnel therein.

21. The container assembly of claim 17, wherein the closure assembly comprises at least one downwardly extending ramp member, and the collection container comprises at least one upwardly extending ramp member configured for cooperating with the at least one downwardly extending ramp member to engage or disengage the closure assembly with the collection container.

22. The container assembly of claim 17, further comprising a conical recess defined within the stopper, wherein the conical recess is in communication with an interior of the collection container when the closure assembly closes the open top portion of the collection container.

23. The container assembly of claim 22, wherein the stopper defines a conical recess extending between a bottom surface and the pierceable portion, and a sampling distance extending between a top surface of the top portion of the cap body and an apex of the conical recess is adapted to position an aspiration hole of a probe assembly at the apex of the conical recess during withdrawal of a specimen from the collection cavity.

24. The container assembly of claim 17, wherein the collection container defines an interior having at least one capillary channel disposed therein.

25. The container assembly of claim 17, wherein the pierceable portion is pierceable by a cannula while the closure assembly closes the open top end of the collection container.

26. The container assembly of claim 25, wherein the pierceable portion is adapted to remove vestige from the cannula upon withdrawal of the cannula from an interior of the collection container.

27. The closure of claim 1, wherein the stopper further comprises an upper portion and a lower portion, the pierceable portion is disposed between the upper portion and the lower portion, and the lower portion defines a funnel-shaped recess.

28. The closure of claim 11, wherein the stopper further comprises an upper portion and a lower portion, the pierceable portion is disposed between the upper portion and the lower portion, and the lower portion defines a funnel-shaped recess.

29. The container assembly of claim 17, wherein the stopper further comprises an upper portion and a lower portion, the pierceable portion is disposed between the upper portion and the lower portion, and the lower portion defines a funnel-shaped recess.

30. The closure of claim 11, wherein the cap body is formed from a first molding material and the stopper is formed from a pierceable second molding material, the second molding material being different than the first molding material.

31. The container assembly of claim 17, wherein the cap body is formed from a first molding material and the stopper is formed from a pierceable second molding material, the second molding material being different than the first molding material.

32. The closure of claim 1, wherein the stopper is in continuous contact with the cap body.

33. The closure of claim 32, wherein the stopper is integrally connected with the cap body.

34. The closure of claim 32, wherein the stopper is permanently connected with the cap body.

35. The closure of claim 1, wherein the entirety of the stopper is disposed within the cavity of the cap body.

36. The closure of claim 11, wherein the entirety of the stopper is disposed within the cavity of the internal annular skirt.

37. The container assembly of claim 17, wherein the entirety of the stopper is disposed within the cavity of the cap body.

38. The closure of claim 1, wherein the cap body defines an elliptical-shaped cut out portion.

39. The closure of claim 11, wherein the external annular skirt defines an elliptical-shaped cut out portion.

40. The container assembly of claim 17, wherein the cap body defines an elliptical-shaped cut out portion.

41. The closure of claim 1, wherein only the cap body defines the permanent cavity.

42. The closure of claim 11, wherein only the internal annular skirt of the closure assembly defines the permanent cavity.

43. The container assembly of claim 17, wherein only the cap body defines the permanent cavity.

* * * * *